(12) United States Patent
Suttin et al.

(10) Patent No.: US 10,905,504 B2
(45) Date of Patent: Feb. 2, 2021

(54) ROBOTIC DEVICE FOR DENTAL SURGERY

(71) Applicant: BIOMET 3I, LLC, Palm Beach Gardens, FL (US)

(72) Inventors: Zachary B Suttin, West Palm Beach, FL (US); Stephen S. Porter, West Palm Beach, FL (US)

(73) Assignee: Biomet 3I, LLC, Palm Beach Gardens, FL (US)

( * ) Notice: Subject to any disclaimer, the term of this patent is extended or adjusted under 35 U.S.C. 154(b) by 254 days.

(21) Appl. No.: 15/170,190

(22) Filed: Jun. 1, 2016

(65) Prior Publication Data
US 2016/0354169 A1  Dec. 8, 2016

Related U.S. Application Data

(60) Provisional application No. 62/170,038, filed on Jun. 2, 2015.

(51) Int. Cl.
*A61B 34/32* (2016.01)
*A61B 34/20* (2016.01)
(Continued)

(52) U.S. Cl.
CPC .......... *A61B 34/32* (2016.02); *A61B 17/3211* (2013.01); *A61B 34/20* (2016.02);
(Continued)

(58) Field of Classification Search
CPC ......... A61B 34/32; A61B 34/20; A61B 34/30; A61B 17/13211; A61B 2034/102; A61B 2034/105; A61C 1/082; A61C 8/0089
(Continued)

(56) References Cited

U.S. PATENT DOCUMENTS 4,182,312 A  1/1980 Mushabac
4,997,369 A * 3/1991 Shafir ................ A61C 13/0004
                                                 33/503
(Continued)

FOREIGN PATENT DOCUMENTS

CN      107205795 A     9/2017
WO   WO-2011132183 A1  10/2011
(Continued)

OTHER PUBLICATIONS

"International Application Serial No. PCT/US2015/058881, International Search Report dated Feb. 11, 2016", 6 pgs.
(Continued)

*Primary Examiner* — Heidi M Eide
*Assistant Examiner* — Drew S Folgmann
(74) *Attorney, Agent, or Firm* — Schwegman Lundberg & Woessner, P.A.

(57) ABSTRACT

A robotic system includes a base, a grounding arm, a working arm, and one or more sensors. The grounding arm extends from the base and is configured to be coupled to a fixed structure within the mouth of the patient for establishing an origin for the robotic system. The working arm extends from the base and is configured to be coupled with one or more tools for use during an installation of a dental implant in the mouth. The one or more sensors are for monitoring positions of the grounding arm and/or the working arm and to generate positional data that is used to create a post-operative virtual three-dimensional model of at least a portion of the mouth of the patient.

19 Claims, 9 Drawing Sheets

(51) Int. Cl.
  *A61B 34/30* (2016.01)
  *A61B 17/3211* (2006.01)
  *A61C 1/08* (2006.01)
  *A61C 8/00* (2006.01)
  *A61B 34/10* (2016.01)

(52) U.S. Cl.
  CPC .............. *A61B 34/30* (2016.02); *A61C 1/082* (2013.01); *A61C 8/0089* (2013.01); *A61B 2034/102* (2016.02); *A61B 2034/105* (2016.02)

(58) Field of Classification Search
  USPC ........ 433/72, 76, 79, 73, 74, 75, 77, 78, 80, 433/82, 108, 109
  See application file for complete search history.

(56) References Cited

U.S. PATENT DOCUMENTS

| | | | |
|---|---|---|---|
| 5,343,391 | A | 8/1994 | Mushabac |
| 8,651,858 | B2 | 2/2014 | Berckmans, III et al. |
| 8,808,000 | B2 * | 8/2014 | Salcedo .................. A61B 1/24 |
| | | | 433/196 |
| 2002/0133095 | A1 | 9/2002 | Mushabac et al. |
| 2009/0253095 | A1 | 10/2009 | Salcedo et al. |
| 2009/0263764 | A1 | 10/2009 | Berckmans, III et al. |
| 2010/0137881 | A1 | 6/2010 | Kamer |
| 2011/0039229 | A1 | 2/2011 | Senia |
| 2012/0064489 | A1 | 3/2012 | Rubbert et al. |
| 2012/0095732 | A1 | 4/2012 | Fisker et al. |
| 2013/0172731 | A1 | 7/2013 | Gole |
| 2014/0080092 | A1 | 3/2014 | Suttin et al. |
| 2014/0080095 | A1 | 3/2014 | Suttin et al. |
| 2014/0178832 | A1 | 6/2014 | Choi et al. |
| 2014/0272797 | A1 | 9/2014 | Prestipino |
| 2015/0057675 | A1 * | 2/2015 | Akeel .................... A61B 19/50 |
| | | | 606/130 |
| 2016/0157964 | A1 | 6/2016 | Suttin et al. |
| 2017/0196654 | A1 * | 7/2017 | Toyoda .............. A61B 17/1673 |

FOREIGN PATENT DOCUMENTS

| | | |
|---|---|---|
| WO | WO-2016093984 A1 | 6/2016 |
| WO | WO-2016196592 A1 | 12/2016 |

OTHER PUBLICATIONS

"International Application Serial No. PCT/US2015/058881, Written Opinion dated Feb. 11, 2016", 8 pgs.

"International Application Serial No. PCT/US2016/035213, International Search Report dated Jul. 27, 2016", 4 pgs.

"International Application Serial No. PCT/US2016/035213, Written Opinion dated Jul. 27, 2016", 7 pgs.

"U.S. Appl. No. 14/932,156, Non Final Office Action dated Jan. 25, 2018", 11 pgs.

"U.S. Appl. No. 14/932,156, Response filed Jan. 9, 2018 to Restriction Requirement dated Nov. 9, 2017", 9 pgs.

"U.S. Appl. No. 14/932,156, Restriction Requirement dated Nov. 9, 2017", 6 pgs.

"European Application Serial No. 15794034.7. Response filed Jan. 31, 2018 to Action dated Jul. 21, 2017", 11 pgs.

"International Application Serial No. PCT/US2016/035213, International Preliminary Report on Patentability dated Dec. 14, 2017", 9 pgs.

"European Application Serial No. 15794034.7, Communication Pursuant to Article 94(3) EPC dated Apr. 26, 2018", 7 pgs.

"U.S. Appl. No. 14/932,156, Response filed Apr. 25, 2018 to Non Final Office Action dated Jan. 25, 2018", 11 pgs.

"U.S. Appl. No. 14/932,156, Final Office Action dated Sep. 7, 2018", 21 pgs.

"European Application Serial No. 15794034.7, Response filed Nov. 6, 2018 to Communication Pursuant to Article 94(3) EPC dated Apr. 26, 2018", 15 pgs.

* cited by examiner

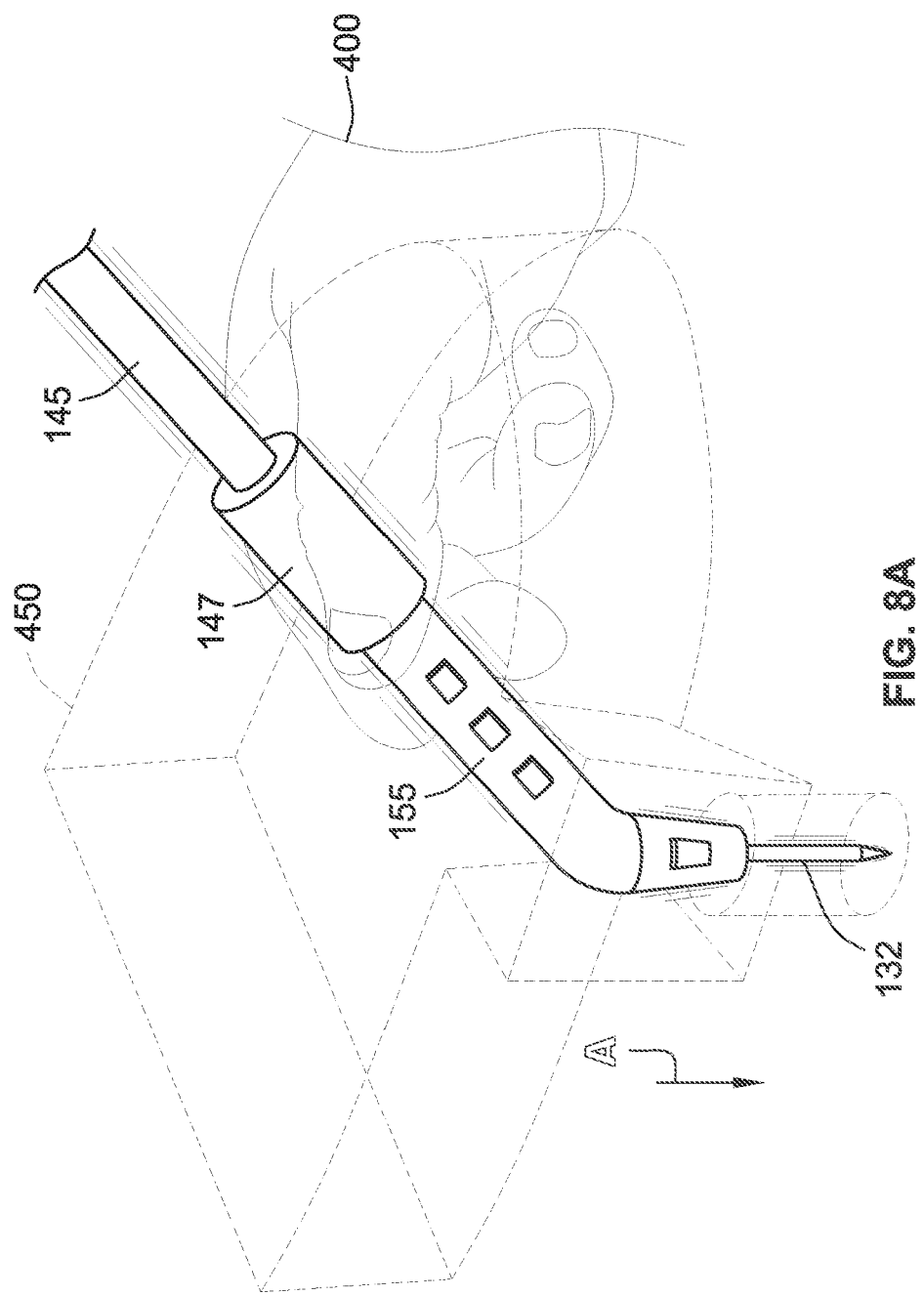

ROBOTIC DEVICE FOR DENTAL SURGERY

CROSS-REFERENCE TO RELATED APPLICATIONS

This application claims the benefit of U.S. Provisional Patent Application Ser. No. 62/170,038, filed on Jun. 2, 2015, the benefit of priority of which is claimed hereby, and which is incorporated by reference herein in its entirety.

FIELD OF THE INVENTION

The present disclosure relates generally to robotic systems and methods of using the same. More particularly, the present disclosure relates to using a robotic system to (i) automatically perform a variety of dental procedures and/or (ii) monitor a manually performed dental procedure, thereby generating positional data of the robotic system that is usable in creating a modified three-dimensional model for use in developing a final and/or temporary dental prosthesis (e.g., crown, abutment, etc.).

BACKGROUND OF THE INVENTION

The dental restoration of a partially or wholly edentulous patient with artificial dentition typically begins with an incision being made through the patient's gingiva to expose the underlying bone. An artificial tooth root, in the form of a dental implant, is placed in the jawbone for osseointegration. The dental implant generally includes a threaded bore configured to receive a retaining screw for holding mating components (e.g., temporary tooth prosthesis, permanent abutment, permanent crown, etc.) thereon. After the dental implant is placed, the gum tissue overlying the dental implant is sutured and heals as the osseointegration process continues.

Once the osseointegration process is complete, the gingival tissue is re-opened to expose an end of the dental implant. A healing component or healing abutment is fastened to the exposed end of the dental implant to allow the gingival tissue to heal therearound. It should be noted that the healing abutment can be placed on the dental implant immediately after the implant has been installed and before osseointegration, thereby, for some situations, combining the osseointegration step and gingival healing step into a one-step process.

At some point thereafter, designing of permanent components to be attached to the dental implant begins. The permanent components are typically referred to as a prosthetic tooth (e.g., permanent abutment plus a permanent crown attached thereto in the shape of a tooth). The design and manufacture of these permanent components requires highly skilled individuals working with models of the mouth of the patient to design components that will look good and function property (e.g., fit between the adjacent teeth, etc.).

While the models used to design the permanent components are typically physical models made from impressions of the mouth of the patient, in recent years, the designing of the permanent components to be attached to the manually installed dental implant has involved the use of computers and virtual three-dimensional models of the mouth of the patient. In order to accurately design permanent components that mate with the manually installed dental implant in a planned manner (i.e., with a planned rotational orientation and a planned vertical dimension of occlusion), precise details about the location and rotational orientation of the manually installed dental implant must be known and incorporated in to the virtual three-dimensional model.

In order to obtain this information, prior systems have used scanning abutments that replace the healing abutment for a short period of time and require an intraoral scan of the mouth of the patient to obtain the required data to create the virtual three-dimensional model. The replacing of the heating abutment with the scanning abutment, even for a short period of time, has disadvantages, such as, added discomfort to the patient having to have additional procedures performed, disruption to the gingival healing process, etc.

However, some other prior systems use coded healing abutments that have scannable features e.g., markers) thereon that when scanned and interpreted, provide the necessary information about the location and orientation of the underlying dental implant to create the virtual three-dimensional model without the need to remove the healing abutment and place a separate scanning abutment in the mouth of the patient. While these systems do not require the removal of the healing abutment to create the virtual three-dimensional model, they still do require the intraoral scanning step, which requires expensive intraoral scanning equipment. The present disclosure is directed to solving these and other needs.

SUMMARY OF THE INVENTION

According to some implementations, a robotic system for use during a dental surgical procedure including installation of a dental implant in a mouth of a patient includes a base; a grounding arm having a first end and a second end, the first end of the grounding arm being coupled to the base, the second end of the grounding arm being configured to be coupled to a fixed structure within the mouth of the patient for establishing an origin for the robotic system relative to the mouth of the patient, the second end of the grounding arm having at least six degrees of freedom relative to the base; a working arm having a first end and a second end, the first end of the working arm extending from the base, the second end of the working arm being configured to be coupled with one or more tools for use during the dental surgical procedure, a portion of the working arm having at least six degrees of freedom relative to the base and being movable to (i) form an opening in bone within the mouth of the patient and (ii) install the dental implant in the formed opening; and one or more sensors to monitor positions of the grounding arm and the working arm, the one or more sensors generating positional data that is used to create a post-operative virtual three-dimensional implant level model of at least a portion of the mouth of the patient.

According to some implementations, a robotic system for use during installation of a dental implant in a mouth of a patient includes a base; a grounding arm extending from the base and being configured to be coupled to a fixed structure within the mouth of the patient for establishing an origin for the robotic system relative to the mouth of the patient; a working arm extending from the base and being configured to be coupled with one or more tools for use during the installation of the dental implant, at least a portion of the working arm being movable to install the dental implant in the mouth of the patient; and one or more sensors to monitor positions of the grounding arm and the working arm, the one or more sensors generating positional data that is used to create a virtual model of at least a portion of the mouth of the patient.

According to some implementations, a method of creating a post-operative virtual model of at least a portion of a mouth of a patient, where the mouth includes a dental implant installed using a robotic system during a dental surgical procedure, includes attaching a rigid grounding member to a fixed position within the mouth of the patient; obtaining a pre-operative virtual model of the mouth of the patient with the rigid grounding member therein; coupling a grounding arm of the robotic system to the rigid grounding member in the mouth of the patient, thereby establishing an origin for the mouth of the patient; moving, as part of the dental surgical procedure, at least a portion of a working arm of the robotic system coupled to a dental-implant-driving tool to install the dental implant in the mouth of the patient; monitoring, during the dental surgical procedure, a position of the grounding arm and the working arm to generate positional data related to the location of the dental-implant-driving tool relative to the established origin; and creating the post-operative virtual model of the at least a portion of the mouth of the patient based on the obtained pre-operative virtual model and the generated positional data.

According to some implementations, a method of automatically shaving alveolar bone in a mouth of a patient using a robotic system includes attaching a rigid grounding member to a fixed position within the mouth of the patient; obtaining a pre-shaved virtual model of the mouth of the patient with the rigid grounding member therein; coupling a grounding arm of the robotic system to the rigid grounding member in the mouth of the patient, thereby establishing an origin for the mouth of the patient; developing a plan for automatically moving a bone-cutting tool relative to the established origin to shave a portion of the alveolar bone in the mouth of the patient; attaching the bone-cutting tool to a working arm of the robotic system; and executing the developed plan by automatically moving the bone-cutting tool via the working arm of the robotic system, thereby shaving the alveolar bone in the mouth of the patient according to the developed plan such that an exposed ridge of the alveolar bone in the mouth of the patient is sufficiently widened for drilling and receiving a dental implant therein.

According to some implementations, a method of installing a dental implant in a mouth of a patient using a robotic system includes developing a plan for installing the dental implant in the mouth of the patient, the developed plan including (i) a first sub-plan for shaving an exposed portion of bone in the mouth with a first toot, thereby creating a sufficiently widened portion of the bone for receiving the dental implant therein, (ii) a second sub-plan for forming an opening in the sufficiently widened portion of the bone to receive the dental implant with a second toot, and (iii) a third sub-plan for installing the dental implant within the opening with a third tool; establishing an origin for the mouth of the patient by coupling a grounding arm of the robotic system to a rigid grounding member in the mouth of the patient; and executing the plan by: (A) coupling the first tool to a working arm of the robotic system and shaving the exposed portion of the bone in the mouth of the patient by moving at least a portion of the working arm according to the first sub-plan; (B) coupling the second tool to the working arm of the robotic system and forming the opening in the bone in the mouth of the patient by moving the at least a portion of the working arm according to the second sub-plan; and (C) coupling the third tool and the dental implant to the working arm of the robotic system and installing the dental implant into the opening in the bone in the mouth of the patient by moving the at least a portion of the working arm according to the third sub-plan.

According to some implementations, a method of shaving alveolar bone in a mouth of a patient using a robotic system includes establishing an origin for the mouth of the patient by coupling a grounding arm of the robotic system to a rigid grounding member in the mouth of the patient; determining an invisible boundary wall to be established around a pre-determined location in the mouth of the patient; coupling a bone-cutting tool to a working arm of the robotic system; moving at least a portion of the working arm of the robotic system to shave the alveolar bone in the mouth of the patient; during the moving, automatically enforcing the determined invisible boundary wall by preventing the working arm of the robotic system from being moved in a manner that would cause the bone-cutting tool to be moved past the determined invisible boundary wall; and monitoring, during the moving, a position of the grounding arm and the working arm to generate positional data related to the location of the bone-cutting tool relative to the established origin.

According to some implementations, a method of automatically preparing a tooth in a mouth of a patient to receive a custom crown using a robotic system includes attaching a rigid grounding member to a fixed position within the mouth of the patient; obtaining a pre-shaped virtual model of the mouth of the patient with the rigid grounding member therein; coupling a grounding arm of the robotic system to the rigid grounding member in the mouth of the patient, thereby establishing an origin for the mouth of the patient; developing a plan for automatically moving one or more tools relative to the established origin to shape the tooth in the mouth of the patient to receive the custom crown; and in response to a working arm of the robotic system being coupled with at least one of the one or more tools, implementing the developed plan by automatically moving at least a portion of the working arm according to the developed plan, thereby shaping the tooth in the mouth of the patient such that the tooth is substantially shaped according to the developed plan.

According to some implementations, a method of preparing a tooth in a mouth of a patient to receive a custom crown using a robotic system includes attaching a rigid grounding member to a fixed position within the mouth of the patient; obtaining a pre-shaped virtual model of the mouth of the patient with the rigid grounding member therein; determining an invisible boundary wall to be established around the tooth in the mouth to be shaped; coupling a grounding arm of the robotic system to the rigid grounding member in the mouth of the patient, thereby establishing an origin for the mouth of the patient; in response to a working arm of the robotic system being coupled with a shaping tool, manually moving at least a portion of the working arm to shape the tooth in the mouth of the patient; automatically enforcing the determined invisible boundary wall by preventing the working arm from being moved in a manner that would cause a cutting portion of the shaping tool to move outside of the determined invisible boundary wall; monitoring, during the moving, a position of the grounding arm and the working arm to generate positional data related to the location of the cutting portion of the shaping tool relative to the established origin; and creating a post-shaped virtual model of at least a portion of the mouth of the patient based on the obtained pre-shaped virtual model and the generated positional data, the at least a portion of the mouth including the shaped tooth.

According to some implementations, a method of preparing a tooth in a mouth of a patient to receive a custom crown using a robotic system includes coupling a grounding arm of the robotic system to the mouth of the patient, thereby establishing an origin for the mouth of the patient; in response to a working arm of the robotic system being coupled with a shaping tool, manually moving at least a portion of the working arm to shape the tooth in the mouth of the patient; monitoring, during the moving, a position of the grounding arm and the working arm to generate positional data related to the location of a cutting portion of the shaping tool relative to the established origin; and creating a post-shaped virtual model of at least a portion of the mouth of the patient based at least in part on the generated positional data.

According to some implementations, a method of modifying a denture to be coupled with a plurality of dental implants in a mouth of a patient as a hybrid prosthesis using a robotic system includes attaching a first rigid grounding member to a fixed position within the mouth of the patient and attaching a second rigid grounding member to the denture; obtaining a pre-operative virtual model of the mouth of the patient with the first rigid grounding member and the denture therein; removing the denture, with the second rigid grounding member attached thereto, from the mouth of the patient; establishing an origin for the mouth of the patient by coupling a grounding arm of the robotic system to the first rigid grounding member in the mouth of the patient; using a working arm of the robotic system coupled to a dental-implant-driving tool, installing the plurality of dental implants in the mouth of the patient; monitoring, during the installing, a position of the grounding arm and the working arm to generate positional data related to the location of the dental-implant-driving tool relative to the established origin; creating a post-operative virtual model of at least a portion of the mouth of the patient based on the obtained pre-operative virtual model and the generated positional data; based at least in part on the post-operative virtual model, developing a plan for automatically modifying the denture such that the denture can be coupled with the installed plurality of dental implants; coupling the grounding arm of the robotic system to the second rigid grounding member attached to the denture; and using the working arm of the robotic system coupled to a drill-bit tool, modifying the denture by creating a plurality of holes such that the denture can be coupled with the installed plurality of dental implants as the hybrid prosthesis.

According to some implementations, a method of modifying a denture into a hybrid prosthesis using a robotic system includes obtaining a pre-operative virtual model of the mouth of the patient with the denture therein; removing the denture from the mouth of the patient; installing a plurality of dental implants in the mouth of the patient using a first tool controlled by the robotic system; monitoring, during the installing, a position of the first tool to generate positional data; creating a post-operative virtual model of at least a portion of the mouth of the patient based on the obtained pre-operative virtual model and the generated positional data; and based at least in part on the post-operative virtual model, modifying the denture by creating a plurality of holes therein using a second tool controlled by the robotic system such that the denture can be coupled with the installed plurality of dental implants as the hybrid prosthesis.

According to some implementations, a method of modifying a denture to be coupled with a plurality of dental implants in a mouth of a patient as a hybrid prosthesis using a robotic system includes obtaining a first virtual model of the mouth of the patient with the denture therein; removing the denture from the mouth of the patient; attaching a first rigid grounding member to a fixed position within the mouth of the patient; obtaining a second virtual model of the mouth of the patient with the first rigid grounding member therein; attaching a second rigid grounding member to the denture outside of the mouth of the patient; obtaining a third virtual model of the denture with the second rigid grounding member attached thereto; establishing an origin for the mouth of the patient by coupling a grounding arm of the robotic system to the first rigid grounding member in the mouth of the patient; using a working arm of the robotic system coupled to a dental-implant-driving tool, installing the plurality of dental implants in the mouth of the patient; monitoring, during the installing, a position of the grounding arm and the working arm to generate positional data related to the location of the dental-implant-driving tool relative to the established origin; creating a fourth virtual model of at least a portion of the mouth of the patient based on the obtained second virtual model and the generated positional data; based at least in part on the first, the third, and the fourth virtual models, developing a plan for automatically modifying the denture such that the denture can be coupled with the installed plurality of dental implants; coupling the grounding arm of the robotic system to the second rigid grounding member attached to the denture; and using the working arm of the robotic system coupled to a drill-bit tool, modifying the denture by creating a plurality of holes such that the denture can be coupled with the installed plurality of dental implants as the hybrid prosthesis.

According to some implementations, a method of manufacturing a patient specific temporary prosthesis (PSTP) for use in manufacturing a permanent prosthesis for attachment to a dental implant installed in a mouth of a patient includes establishing an origin for a PSTP blank by coupling a grounding arm of a robotic system to the PSTP blank via a fixture; using a working arm of the robotic system coupled to a sculpting tool, modifying the PSTP blank such that the PSTP blank is transformed into the PSTP having a tooth-like shape suitable for attachment to the dental implant installed in the mouth of the patient; monitoring, during the modifying, a position of the grounding arm and the working arm to generate positional data related to the location of the sculpting tool relative to the established origin; and based at least in part on the generated positional data, creating a virtual model of at least a portion of the PSTP.

According to some implementations, a method of manufacturing a patient specific temporary prosthesis (PSTP) for use in manufacturing a permanent prosthesis for attachment to a dental implant installed in a mouth of a patient includes establishing an origin for a PSTP blank by coupling a grounding arm of a robotic system to the PSTP blank via a fixture; using a working arm of the robotic system coupled to a sculpting tool, modifying the PSTP blank such that the PSTP blank is transformed into the PSTP having a tooth-like shape suitable for attachment to the dental implant installed in the mouth of the patient; monitoring, during the modifying, a position of the grounding arm and the working arm to generate positional data related to the location of the sculpting tool relative to the established origin; based at least in part on the generated positional data, creating a virtual model of at least a portion of the PSTP; attaching the PSTP to the dental implant in the mouth of the patient; permitting gingival tissue surrounding the PSTP to heal in the mouth of the patient; in response to the healed gingival tissue surrounding the PSTP in the mouth of the patient satisfying a threshold, manufacturing the permanent prosthesis as a replica of the PSTP using the created virtual model; in response to the healed gingival tissue surrounding the PSTP in the mouth of the patient not satisfying the threshold: (i) physically modifying the PSTP; (ii) scanning the modified PSTP to obtain a modified virtual model of at least a portion of the modified PSTP; and (iii) manufacturing the permanent prosthesis as a replica of the modified PSTP using the obtained modified virtual model.

A method of using a robotic system to automatically create a socket in a jawbone of a patient for receiving a dental implant therein including attaching a rigid grounding member to a fixed position within the mouth of the patient A pre-operative virtual model of the mouth of the patient with the rigid grounding member therein is obtained. A grounding arm of the robotic system is coupled to the rigid grounding member in the mouth of the patient, thereby establishing an origin for the mouth of the patient. A plan for automatically moving two or more of a plurality of surgical tools relative to the established origin is developed to create the socket in the jawbone of the patient. A first one of the plurality of surgical tools is attached to a working arm of the robotic system. A first portion of the developed plan is executed by automatically moving the first one of the plurality of surgical tools via the working arm of the robotic system, thereby starting to create the socket in the jawbone of the patient according to the developed plan. Data is received from one or more sensors of the robotic system indicative of at least one of a torque or a force required to implement the first portion of the developed plan. A second portion of the developed plan is modified based on the received data. The modified second portion of the developed plan is executed by automatically moving a second one of the plurality of surgical tools via the working arm of the robotic system, thereby completing the socket in the jawbone of the patient according to the modified plan.

A method of using a robotic system includes developing a plan for automatically moving one or more of a plurality of surgical tools relative to an established origin of the robotic system to perform a surgical procedure in a mouth of a patient. A first one of the plurality of surgical tools is attached to a working arm of the robotic system. A first portion of the developed plan is executed. During the execution of the first portion of the developed plan, data is received from one or more sensors of the robotic system. A second portion of the developed plan is modified based on the received data.

Additional aspects of the present disclosure will be apparent to those of ordinary skill in the art in view of the detailed description of various implementations, which is made with reference to the drawings, a brief description of which is provided below.

BRIEF DESCRIPTION OF THE DRAWINGS

The foregoing and other advantages of the disclosure will become apparent upon reading the following detailed description and upon reference to the drawings.

FIG. 8A is an illustrative perspective view of the surgical tool coupled to the working arm of the robotic system bumping into an invisible barrier wall according to some implementations of the present disclosure;

Figure 1:
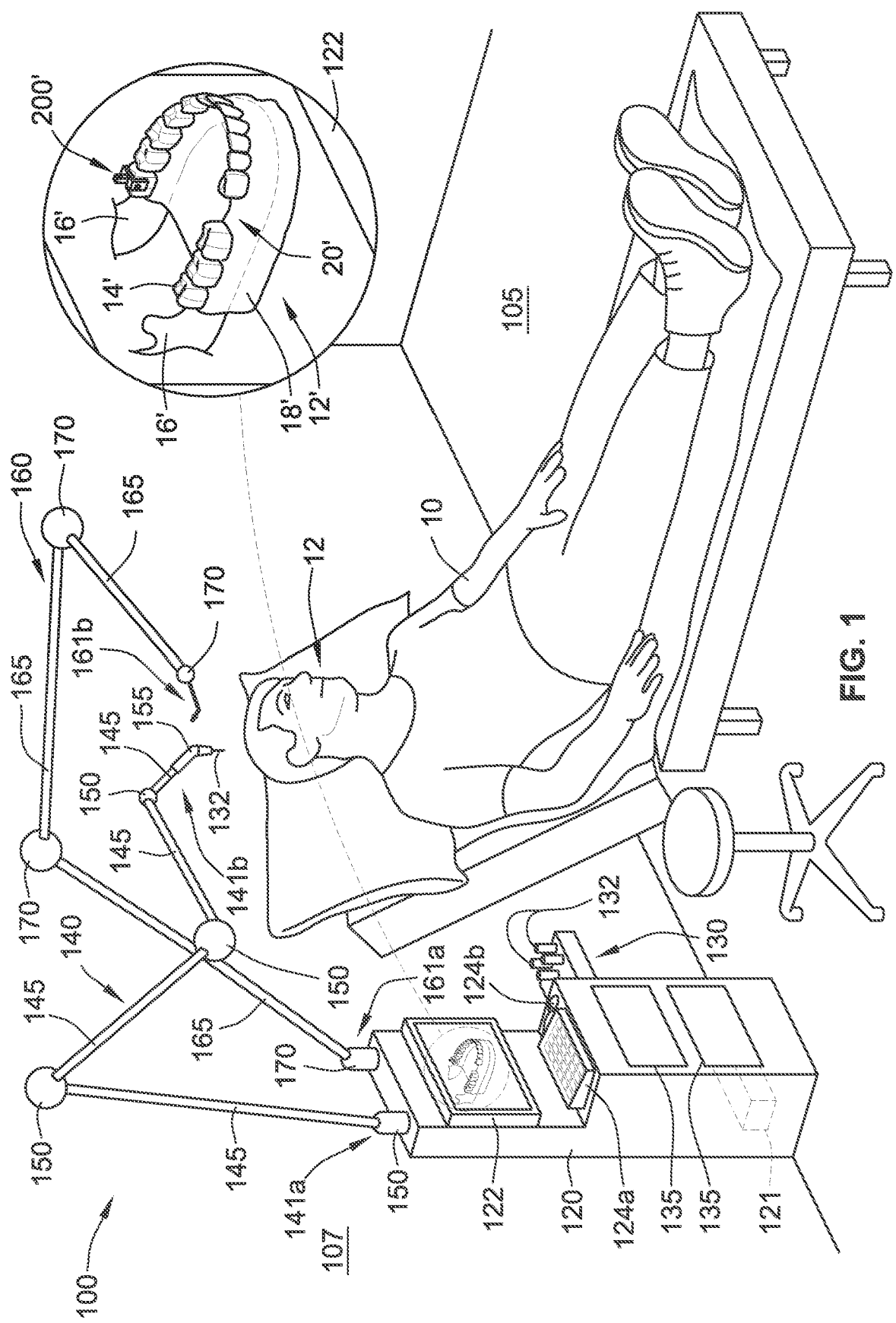
FIG. 1 is a perspective view of a robotic system having a working arm and a grounding arm according to some implementations of the present disclosure.

While the present disclosure is susceptible to various modifications and alternative forms, specific embodiments have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DESCRIPTION OF ILLUSTRATIVE EMBODIMENTS

Referring to FIG. 1, a robotic system 100 of the present disclosure can be used in a variety of manners to perform a variety of surgical and/or non-surgical procedures. Once the robotic system 100 is registered to a patient 10 and loaded with a pre-determined surgical plan, the robotic system 100 is ready to automatically carry out one or more surgical procedures or portions thereof. By automatically, it is meant that the robotic system can, without interruption or input from a human (e.g., other than registering the robotic system 100, loading the pre-determined surgical plan, and in some implementations hitting a start button), perform a surgical procedure or portion thereof.

Additionally, the robotic system 100 can be manually manipulated by, for example, an oral surgeon to be used in performing one or more surgical procedures. Manually performing a surgical procedure using the robotic system 100 aids the surgeon as compared to performing a manually procedure without the robotic system 100 as the robotic system 100 supports the weight of the tools (e.g., tool 155 and surgical tool-bits 132 coupled thereto) used by the surgeon during the often lengthy surgery. Further, the robotic system 100 can be configured to aid the surgeon by preventing the surgeon from moving a surgical tool-bit 132 of the robotic system 100 in a manner that is inconsistent with a general plan or outline for the procedure. For example, an invisible barrier wall (e.g., invisible barrier wall 450 shown in FIGS. 8A and 8B) and/or area can be established prior to a procedure being conducted such that the robotic system 100 prevents manual manipulation of the tool 155 and tool-bit 132 coupled thereto in a manner that would cause the surgical tool-bit 132 to move past the invisible barrier wall/area 450 (e.g., and into a nerve, the wrong tooth, the palate of the mouth of the patient, the cheek of the patient, etc.). Further, the robotic system 100 can implement haptic feedback to indicate to a manual user 400 (FIGS. 7, 8A, 8B) of the robotic system 100 that the user 400 (e.g., the surgeon) is attempting to move the surgical tool outside of the accepted working space (e.g., past the invisible barrier watt/area 450). For example, the robotic system 100 can vibrate the tool 155 and/or make an audible noise to indicate that the surgeon 400 is attempting to move the tool 155 and surgical tool-bit 132 coupled thereto past the predefined limits for the particular procedure (see FIGS. 8A and 8B). Further, the robotic system 100 can improve a surgeon's fidelity by increasing the resolution with which the surgeon can operate as compared to a surgeon not using the robotic system 100. That is, using the robotic system 100, the surgeon is able to move surgical tools coupled thereto with a higher degree of accuracy and in relatively smaller increments (i.e., higher resolution) as compared to the accuracy and increment size the surgeon can move surgical tools without using the robotic system 100.

Figure 8B:
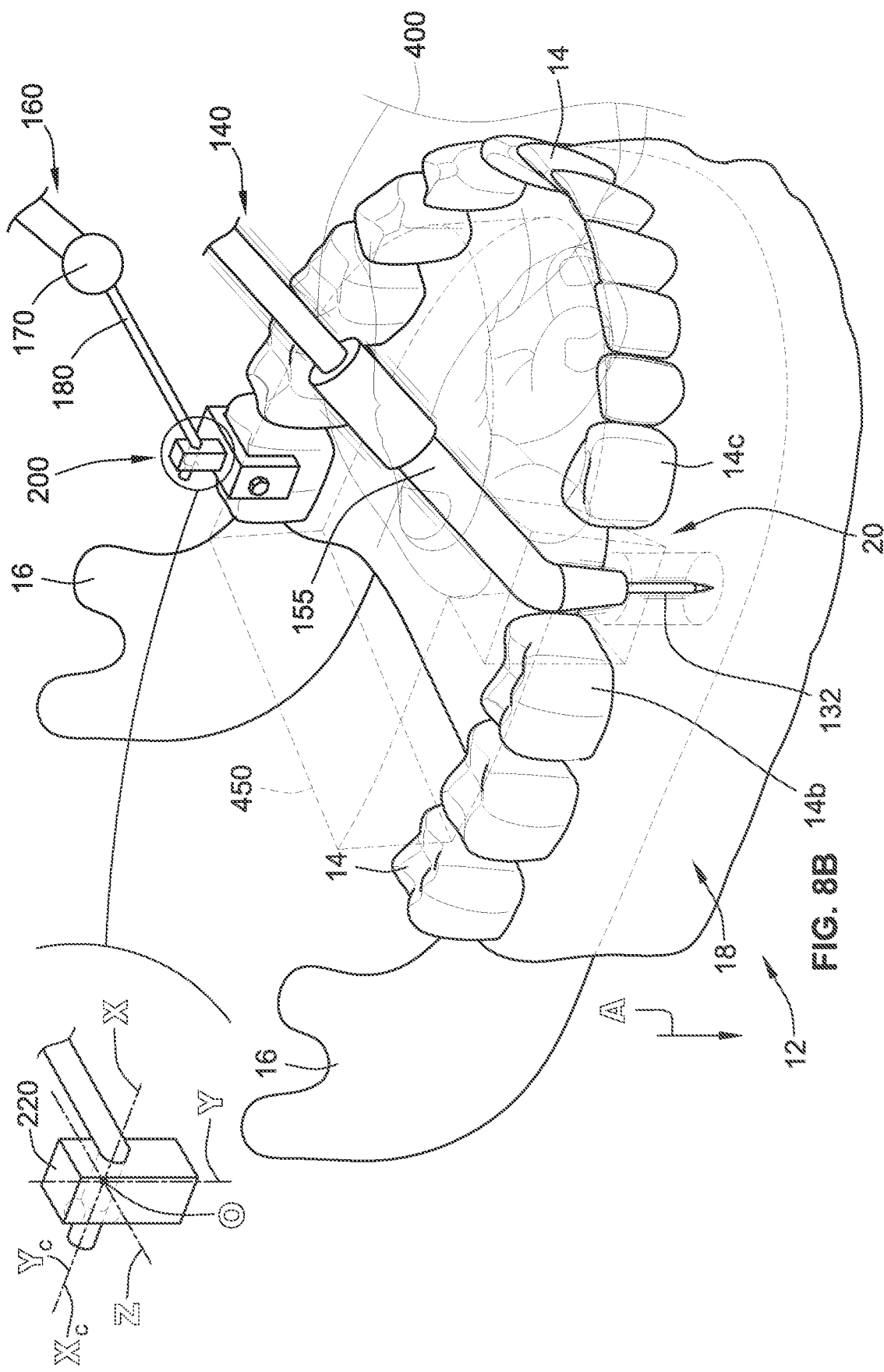
FIG. 8B is the illustrative perspective view of FIG. 8A overlaid on top of the perspective view of FIG. 7 illustrating a use of the invisible barrier wall during the manual performance of a surgical procedure according to some implementations of the present disclosure.
Figure 9:
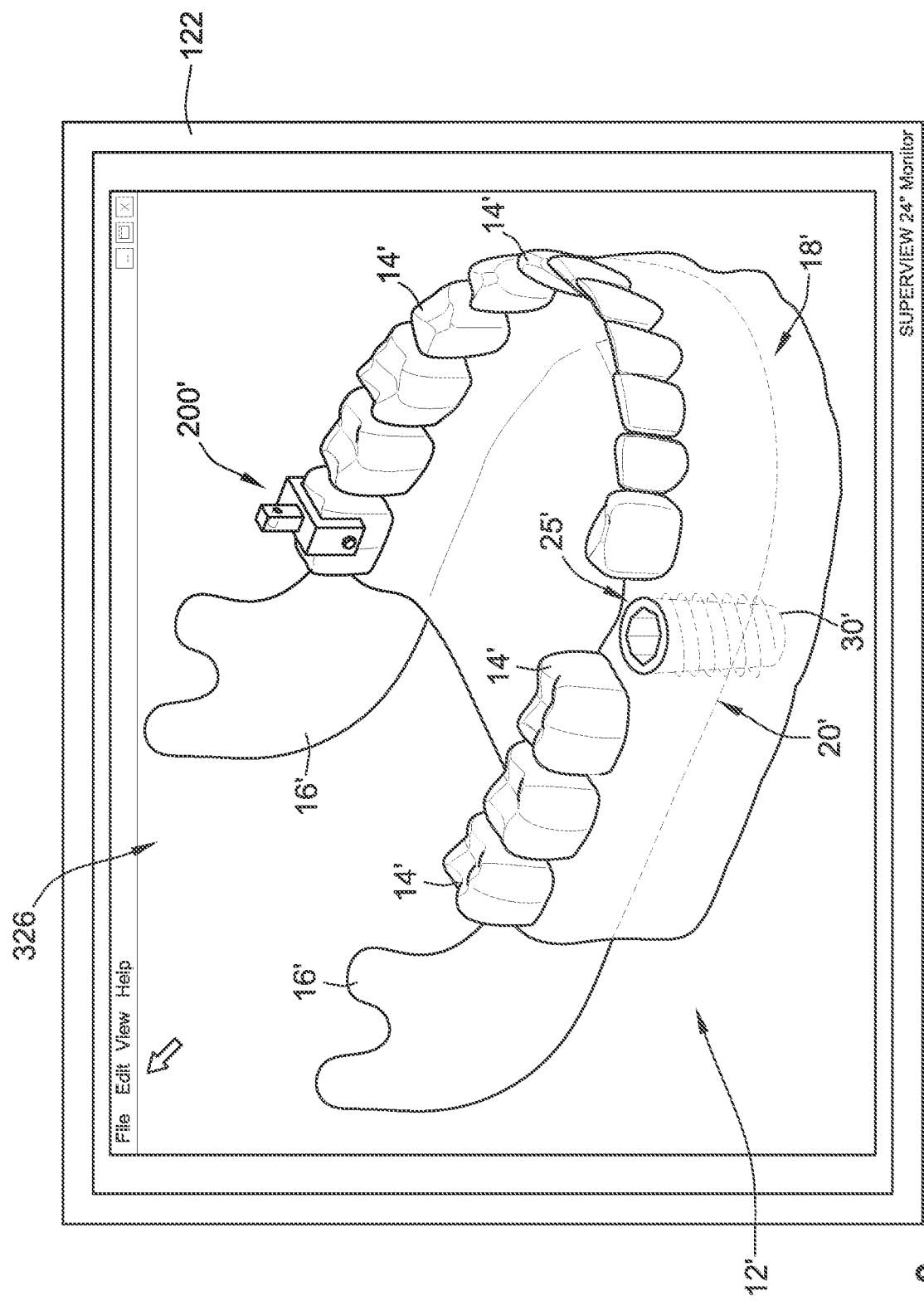
FIG. 9 illustrates a modified or post-operative virtual three-dimensional model of a mouth of a patient displayed on a display device of the robotic system of FIG. 1 according to some implementations of the present disclosure.

Further, during manual manipulation of the robotic system 100, the robotic system 100 can monitor movements of the robotic system 100 and develop a positional data set indicative of the performed procedure. That is, the robotic system 100 can trace/follow a path taken by the tool 155 and/or by the surgical tool-bit 132 coupled thereto (or at least a tip portion of the surgical tool-bit 132) and record data indicative of that traced path. As such, with knowledge of the geometry of the used surgical tool-bit(s) 132 and an established origin, O, (see FIGS. 4 and 8B) for the mouth 12 of the patient 10 and/or of the robotic system 100, the final patient situation can be determined (e.g., a post-operative virtual three-dimensional model 326 of at least a portion of the mouth 12 of the patient 10 as modified during the procedure as shown in FIG. 9). For example, if the robotic system 100 is used to remove bone, the positional data collected by the robotic system 100 would be indicative of where the bone removal tool-bit 132 physically traveled/went relative to the established origin, O, of the mouth during the procedure (e.g., which is related to the bone in the mouth 12 of the patient 10) and can thereby be used to develop a post-operative virtual three-dimensional model (similar to the post-operative virtual three-dimensional model 326 shown in FIG. 9) of at least a portion of the mouth 12 of the patient 10 illustrating the removed bone. This virtual three-dimensional model is thus created without having to take a post-operational intraoral scan of the patient 10—sparing the patient 10 this added scanning step.

Additional details on the robotic system 100 and uses of the robotic system 100 are described below in various Sections herein. White the disclosure is broken into these Sections including various implementations having described elements, any portion and/or any element contained in any Section and/or any implementation can be combined and/or modified with any portion and/or any element in any other Section and/or any other implementation described herein.

Components and General Operation Robotic System 100

As shown in FIG. 1, the robotic system 100 includes a base 120, a working arm 140, and a grounding arm 160. The base 120 can also be referred to as a cabinet for housing a multitude of elements therein, where at least some of the elements housed therein are coupled together to perform one or more functions/operations. The base 120 rests on a ground surface 105 (e.g., a floor of a dental surgical room). The base 120 can be fixed to the ground surface 105 or movable with respect to the ground surface 105. In the implementations when the base 120 is movable with respect to the ground surface 105, a bottom side of the base 120 includes one or more casters or rollers (not shown). Alternatively or additionally to the base 120 resting on and/or being coupled to the ground surface 105, the base can be coupled to a wall surface 107 (e.g., a wall of the dental surgical room). Preferably, the base 120 is mounted to the ground surface 105 and/or the wall 107 to aid in preventing the robotic system 100 from tipping over during use thereof.

The base 120 houses and/or is coupled to/associated with a computer 121, a display device 122, input devices 124a, 124b, a surgical tool tray 130, and storage drawers 135. The computer 121 is communicatively connected with the display device 122, the input devices 124a, 124b, the working arm 140 and the grounding arm 160. The computer 121 can include controllers, processors, memory devices, communication devices (e.g., wireless, wired, etc.), etc. configured to run/execute one or more software programs (e.g., robotic system control software programs, dental surgical planning software programs, abutment design software programs, crown design software programs, etc.). The computer 121 is specially programmed and improved for controlling and/or tracking/tracing the working arm 140 and/or the grounding arm 160 of the robotic system 100. Alternatively, the computer 121 can be a general purpose computer capable of executing specific software to control and/or track the working arm 140 and/or the grounding arm 160 of the robotic system 100.

The input devices 124a, 124b are shown as being a keyboard and a mouse for use in operating the computer 121. Additional input devices can be used such as, for example, a joystick, a wireless or wired electronic pen, a touch screen overlaid on the display device 122, a foot pedal, etc.

The surgical tool tray 130 stores a multitude of surgical tools or surgical tool-bits 132 therein for use in a variety of procedures (e.g., creation of an osteotomy, implant placement, bone shaving, tooth-crown prepping, probing/mechanical sensing, denture modification, provisional restoration shaping, abutment shaping, etc.). While only four surgical tool-bits 132 are shown, any number of surgical tool-hits 132 can be included in the surgical tool tray 130 (e.g., one surgical tool-bit, two surgical tool-bits, ten surgical tool-bits, thirty surgical tool-bits, etc.). The surgical tool-bits 132 can include drill-bit tools (e.g., to create sockets and/or openings in bone), tapping tools (e.g., to create threads in bone sockets/openings), dental-implant-driving tools, rotating mill tools, saw tools, probe tools, mechanical sensing tool-bits, scalpel/knife tools, or any combination thereof. In some implementations, the base 120 stores a multitude of surgical tool trays 130 in one of the storage drawers 135. In such implementations, depending on the procedure being conducted using the robotic system 100, a user (e.g., oral surgeon, clinician, dental assistant, etc.) connects the proper one of the surgical tool trays 130 to the base 120 and puts any extra surgical tool trays 130 back into the storage drawer 135 for future use and/or cleaning. The surgical tools 132 on the surgical tool tray 130 are arranged in a known manner such that the robotic system 100 can cause the working arm 140 to automatically move and pick-up a desired one of the surgical tool-hits 132. In some implementations, to avoid the robotic system 100 picking-up the wrong surgical tool-bit 132, the surgical tool tray 130 is designed such that the surgical tool tray 130 can only connect with the base 120 in one orientation. Further, in some implementations, each surgical tool-bit 132 is designed to only be coupled with one known location on the surgical tool tray 130. Yet in other implementations, an operator of the robotic system 100 manually couples the working arm 140 with a desired one of the surgical tool-bits 132.

The working arm 140 has a first end 141a that extends from the base 120 and a second opposing end 141b that is configured to be coupled with one of the surgical tool-bits 132 via a tool 155 to be used in performing a procedure. Between the first and the second ends 141a,b, the working arm 140 includes a multitude of rigid arm members 145 coupled together by a multitude of flexible joint members 150. Each of the rigid arm members 145 can have a fixed length or be capable of having a variable length, such as, for example, having a telescoping configuration (not shown). Such a telescoping configuration provides added flexibility for the robotic system 100 to reach further from the base 120 during the performance of a procedure. As shown, the working arm 140 is directly coupled to the base 120 via one of the flexible joint members 150, although the working arm 140 can be directly coupled to the base 120 via one of the rigid arm members 145 instead. The rigid arm members 145 can be made of a variety of materials such as, for example, titanium, plastic, steel, of any combination thereof.

Each of the flexible joint members 150 is configured to mate one of the rigid arm members 145 to another one of the rigid arm members 145 or to the base 120. Each of the flexible joint members 150 includes one or more motors therein for causing relative movement of the ones of the rigid arm members 145 mated to the flexible joint member 150. For example, each of the flexible joint members 150 includes an electric servo motor, an electric rotary motor, etc. As such, in response to a command from the computer 121, for example, automatically executing a preplanned surgical procedure, the flexible joint member 150 can cause one of the rigid arm members 145 to rotate/pivot relative to another one of the rigid arm members 145 coupled to the same flexible joint member 150. Depending on the number and/or type of motor(s) in the flexible joint member 150, the relative rotating/pivoting can be one dimensional, two dimensional, or three dimensional. That is, one of the rigid arm members 145 can be caused to rotate/pivot forward and backward relative to the other one of the rigid arm members 145 (e.g., pitching), rotate/pivot left and right relative to the other one of the rigid arm members 145 (e.g., swaying), and/or rotate/pivot side-to-side relative to the other one of the rigid arm members 145 (e.g., rolling).

As shown, the working arm 140 includes four rigid arm members 145 and four flexible joint members 150. With the ability for each of the four flexible joint members 150 to rotate/pivot the rigid arm members 145 mated thereto as described above, the second end 141b of the working arm 140 and/or the tool 155 is able to move with at least six degrees of freedom relative to the base 120 (e.g., three degrees of rotational freedom and three degrees of translational freedom). It is contemplated that the number of rigid arm members 145 and flexible joint members 150 included in the working arm 140 can vary. As the number of the rigid arm members 145 and flexible joint members 150 decreases, so does the flexibility of the working arm 140. Similarly, as the number of the rigid arm members 145 and flexible joint members 150 increases, so does the flexibility of the working arm 140. For example, additional fine-tuning-flexible joint members 150 can be included that have a relatively smaller range of motion to precisely place the tool 155 and the surgical tool-bits 132 coupled thereto in the mouth 12 of the patient 10 in a desired location. Specifically, in some implementations, the surgical tool-bits 132 can be placed with less than a 0.5 millimeter margin of error from a desired target placement. In some other implementations, the surgical tool-bits 132 can be placed with less than a 0.1 millimeter margin of error from a desired target placement.

In addition to each of the flexible joint members 150 including one or more motors therein, each of the flexible joint members 150 includes one or more sensors for sensing the relative positional relationship between the rigid arm member(s) 145 coupled thereto. That is, for example, each one of the flexible joint members 150 includes one or more sensors that can determine the relative angular positional relationship between the two of the rigid arm members 145 coupled thereto relative to an X-Y-Z space having its origin at the center of the flexible joint member 150. Thus, in response to a user of the robotic system 100 moving one of the rigid arm members 145, the one or more sensors in the flexible joint member 150 coupled to the manually moved rigid arm member 145 are configured to sense that movement and generate data representative of the new location of the rigid arm member 145 relative to an origin of the flexible joint member 150 and/or relative to the origin, O, of the robotic system 100 and/or of the mouth 12 of the patient 10. Such data is transmitted (wirelessly and/or via a wire) to the computer 121 for processing. For another example, in response to an operator 400 (FIG. 7) manually moving the second end 141b and/or the tool 155 of the working arm 140 such that some or all of the rigid arm members 145 are moved relative to the base 120, each of the flexible joint members 150 generates data that is transmitted to the computer 121 for processing. The computer 121 is configured to execute a tracing software program and/or algorithm that is able process the data from each of the flexible joint members 150 to determine the location of the second end 141b of the working arm 140 (or any portion of any tool 155 and/or surgical tool-bit 132 coupled thereto) relative one or more established origins, O, for the robotic system 100 and/or for the mouth 12 of the patient 10. As such, the robotic system 100 is capable of tracking movement of the working arm 140.

The grounding arm 160 has a first end 161a that extends from the base 120 and a second opposing end 161b that is configured to be coupled with a rigid grounding member 200 (FIG. 4) to establish the origin, O, for the robotic system 100 and/or for the mouth 12 of the patient 10. Between the first and the second ends 161a,b, the grounding arm 160 includes a multitude of rigid arm members 165 coupled together by a multitude of flexible joint members 170. The rigid arm members 165 are the same as, or similar to, the rigid arm members 145 and the flexible joint members 170 are the same as, or similar to, the flexible joint members 150 described herein.

Figure 2:
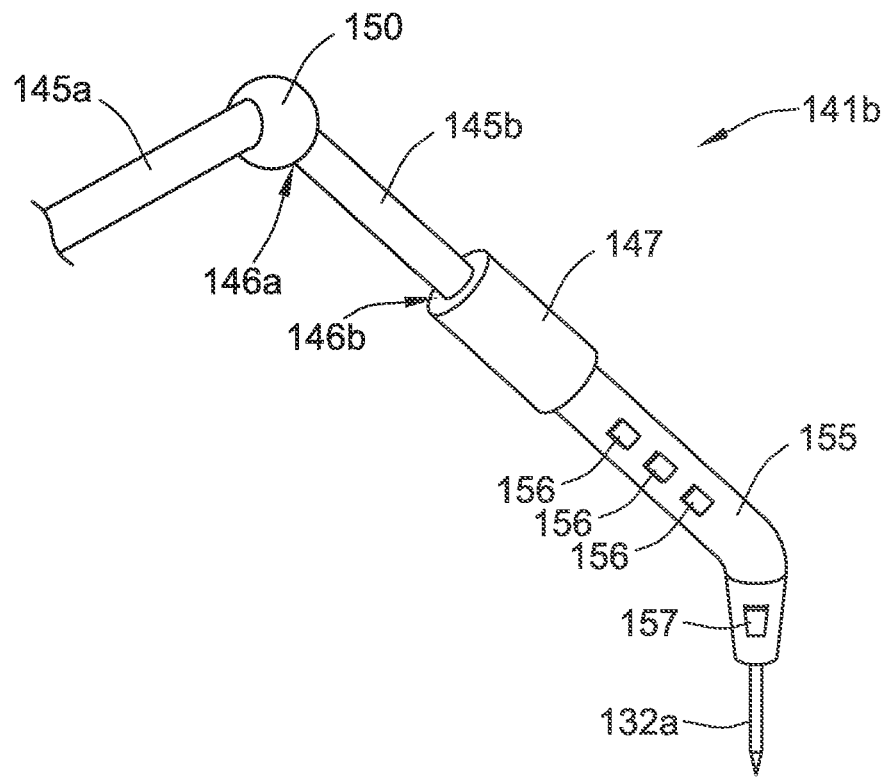
FIG. 2 is a perspective view of a portion of the working arm of the robotic system of FIG. 1 coupled with a surgical tool.

Now referring to FIG. 2, the second end 141b of the working arm 140 is shown in detail. Specifically, a portion of two rigid arm members 145a,b coupled by a flexible joint member 150 is shown. The rigid arm member 145b has a first end 146a coupled with the flexible joint member 150 and a second end 146b that is coupled with a coupler 147. The coupler 147 is rigidly attached to the second end 146b of the rigid arm member 145b and designed to removably receive a portion of the tool 155 therein. As shown in FIG. 2, the tool 155 is a drill or driving tool for rotating a surgical tool-bit 132a. Coupling the tool 155 to the coupler 147 can be purely mechanical and/or electrical. That is, the coupling of the tool 155 with the coupler 147 can include supplying power to the tool 155 through the coupler 147 or the tool 155 can be self-powered (e.g., via one or more disposable and/or rechargeable batteries). The connection between the coupler 147 and the tool 155 can be a press fit connection, a snap-in connection, a threaded connection, a magnetic connection, a friction connection, a tongue and groove connection, or any combination thereof such that the tool 155 is removably and securely coupled to the coupler 147 in a known and repeatable manner. In some implementations, the coupling of the tool 155 with the working arm 140 creates a communicative connection where the tool 155 is able to talk with the computer 121 through the working arm 140, such that the identity of the tool 155 is disclosed to the computer 121. As such, the computer learns the identity and size and shape of the tool 155 which is needed to precisely trace the movements of the tool 155 and any surgical tool-bit 132 coupled thereto. Alternatively, the working arm 140 is designed to only connect with a single tool 155 such that identification of the tool 155 is unnecessary. Yet in further alternative implementations, the robotic system 100 runs a check prior to conducting a procedure to confirm that the correct tool 155 is coupled to the working arm 140.

In some implementations, the tool 155 includes a multitude of buttons 156. The buttons 156 can be preprogrammed and/or programmable to start operation of the tool 155 (e.g., a start/ON button), to end operation of the tool 155 (e.g., a stop/OFF button), to reverse rotation of the tool 155 (e.g., forward/backward rotation), etc. One or more lights (e.g., LEDs) can be included in the tool 155 and positioned adjacent to each button 156 to indicate whether the button 156 is activated or not. In some implementations, the tool 155 includes a release button or mechanism 157 for use in aiding in the removal of the surgical tool-bit 132a from the tool 155. In other implementations, the surgical tool-bit 132a can simply be pulled out of the tool 155 without having to press the release button 157.

Figure 3:
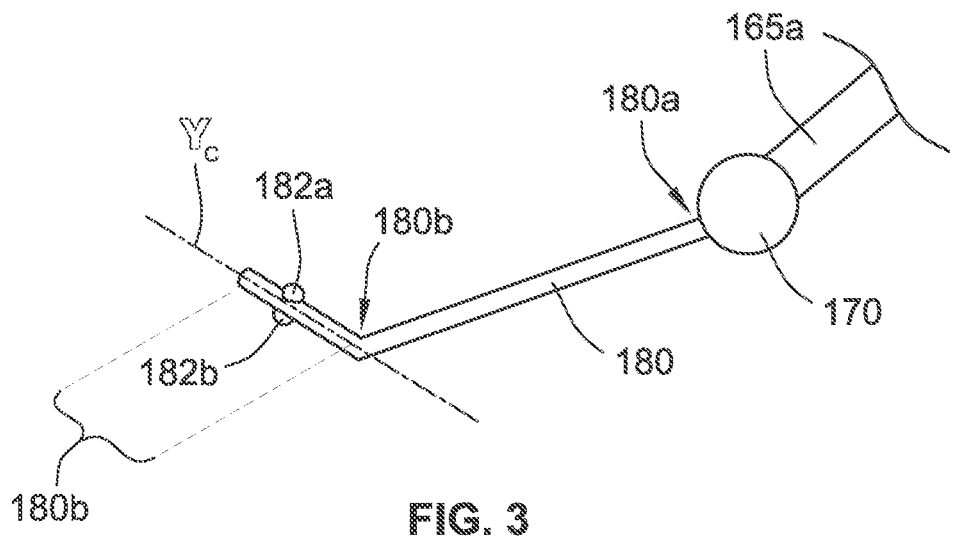
FIG. 3 is a perspective view of a portion of the grounding arm of the robotic system of FIG. 1.

Now referring to FIG. 3, the second end 161b of the grounding arm 160 is shown in detail. Specifically, a portion of a rigid arm member 165a is coupled by a flexible joint member 170 to a grounding probe 180. The grounding probe 180 has a first end 180a coupled with the flexible joint member 170 and a second end 180b designed to couple with the rigid grounding member 200 (FIG. 4) in a removable and repeatable fashion. As shown in FIG. 3, the second end 180b of the grounding probe 180 includes a pair of biased locking bearings 180a,b. The locking bearings 182a,b are biased outward away from a central axis, $Y_C$, of the second end 180b of the grounding probe 180. As such, the locking bearings 182a,b can be forced inward toward the central axis, $Y_C$, to allow the second end 180b of the grounding probe 180 to be slid into a receiving bore 222 of the rigid grounding member 200 (FIG. 4) in a removable and repeatable fashion.

Registering the Robotic System 100 to the Mouth 12 of the Patient 10 Using the Rigid Grounding Member 200

Figure 4:
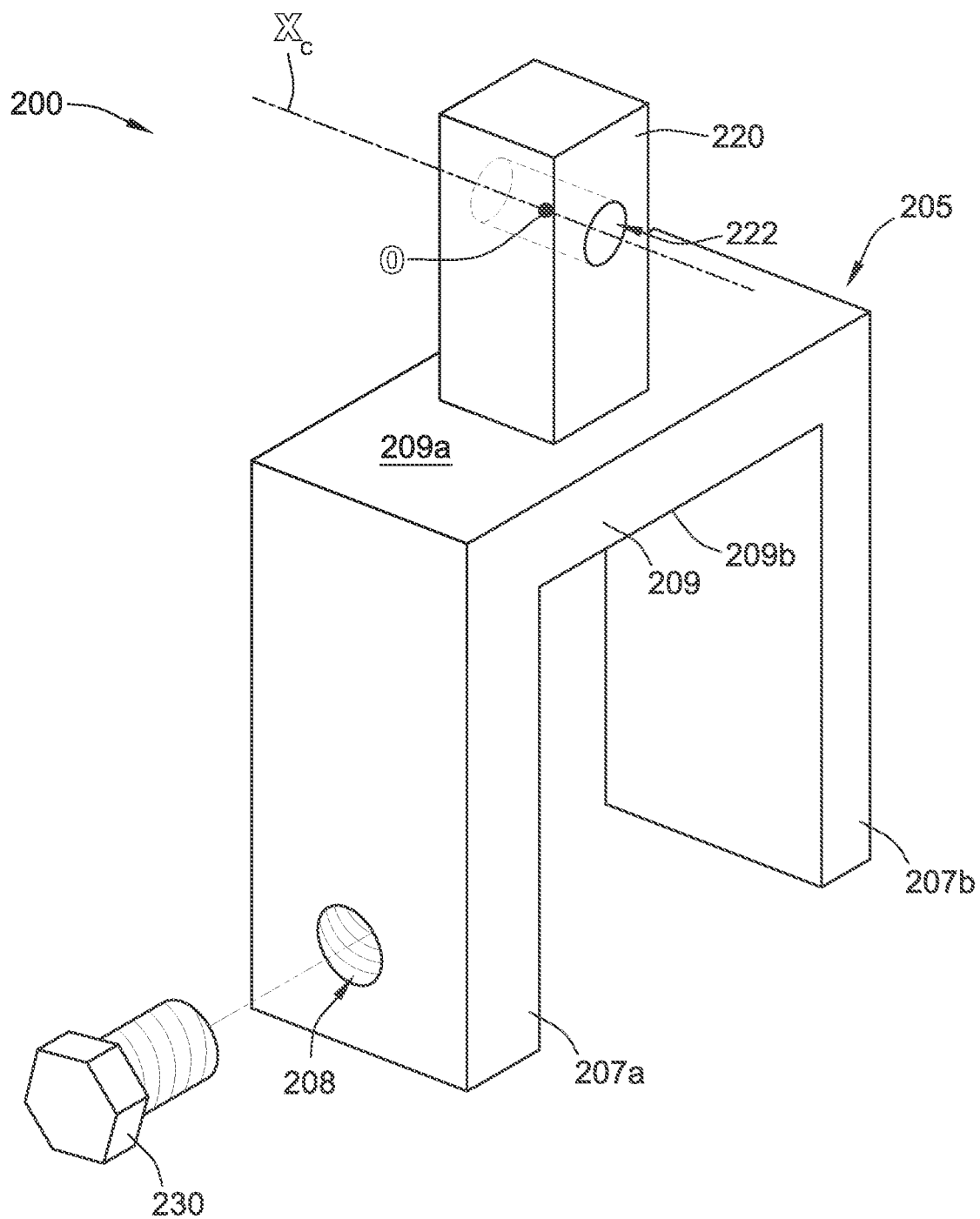
FIG. 4 is a perspective view of a rigid grounding member to be coupled with a mouth of a patient for use with the robotic system of FIG. 1.

Referring to FIG. 4, the rigid grounding member 200 is shown as including a body 205 and a coupling post 220. The body 205 includes a first leg 207a and a second leg 207b coupled together by a base 209 therebetween. The base has an upper surface 209a and a bottom surface 209b. Protruding generally upward from the upper surface 209a of the base 209 is the coupling post 220. The body 205 and the coupling post 220 can be two separate and distinct parts that are attached together or they can be integrally formed as a monolithic component. The coupling post 220 includes the receiving bore 222 therein for receiving the second end 180b of the grounding probe 180 therethrough when grounding the grounding arm 160 of the robotic system 100 to the mouth 12 of the patient 10 (e.g., when the rigid grounding member 200 is installed in the mouth 12 of the patient 10). The receiving bore 222 has a central axis, $X_C$, along which the origin, O, for the robotic system 100 and/or the mouth 12 of the patient 10 can be established. In some implementations, the origin, O, is established at a center of the receiving bore along the central axis, $X_C$. In some alternative implementations, the origin, O, is established at any point along the central axis, $X_C$, for example, at either end opening of the receiving bore 222.

The first leg 207a includes a threaded throughbore 208 that receives a fastener 230 (e.g., surgical dental screw, dental bolt, etc.). While not shown, the second leg 207b can also include a threaded throughbore the same as, or similar to, the threaded throughbore 208 for receiving the fastener 230 therein and/or another fastener (not shown). While the rigid grounding member 200 is shown as having a specific shape and size, various other shapes, sizes, and arrangements for the rigid grounding member 200 are contemplated, such that the rigid grounding member 200 can be attached to the mouth 12 of the patient 10 and provide a means for coupling the grounding probe 180 thereto in a removable and repeatable fashion.

Figure 5:
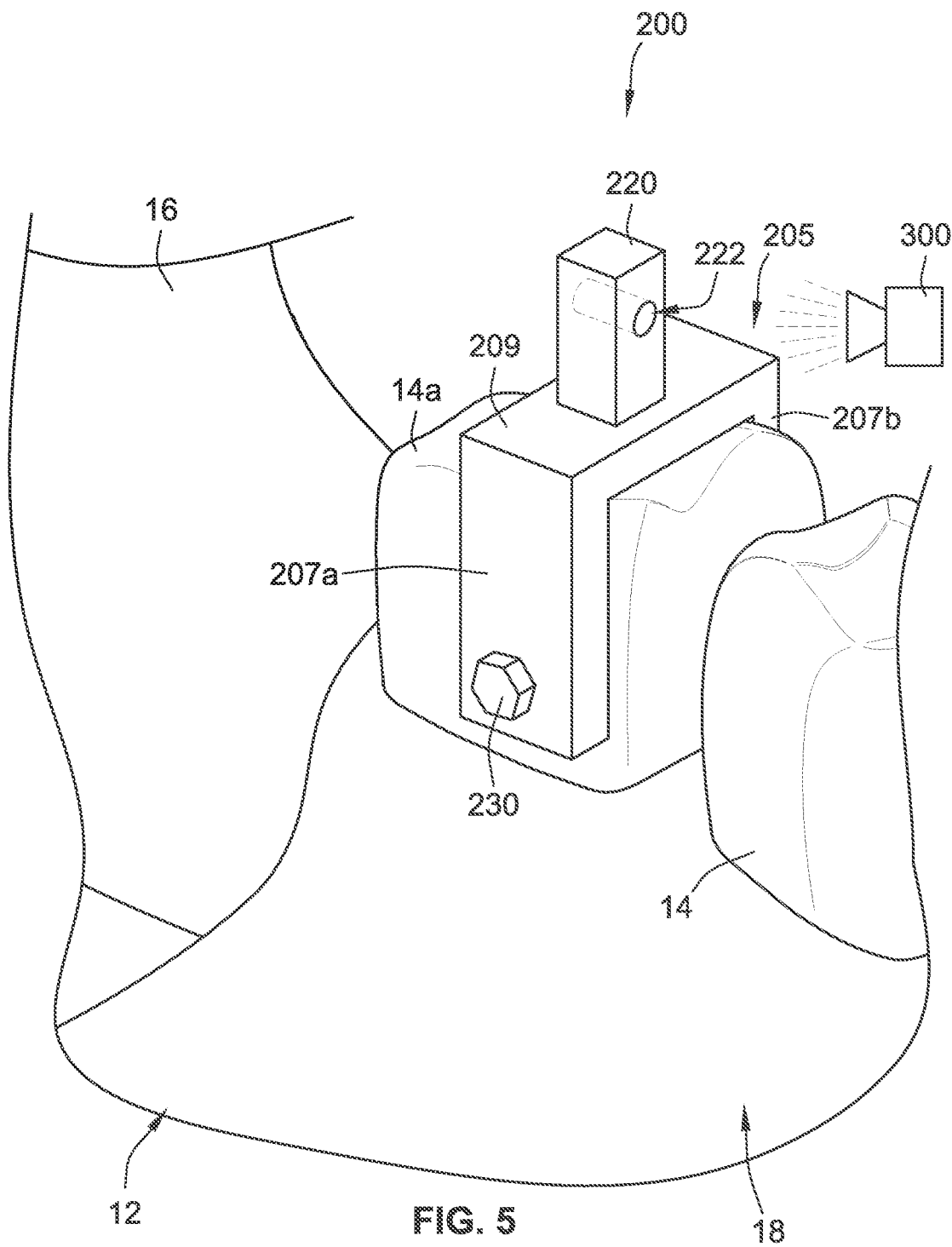
FIG. 5 is a perspective view of the rigid grounding member of FIG. 4 being coupled to a mouth of a patient and a scanner for scanning the mouth of the patient.
Figure 6:
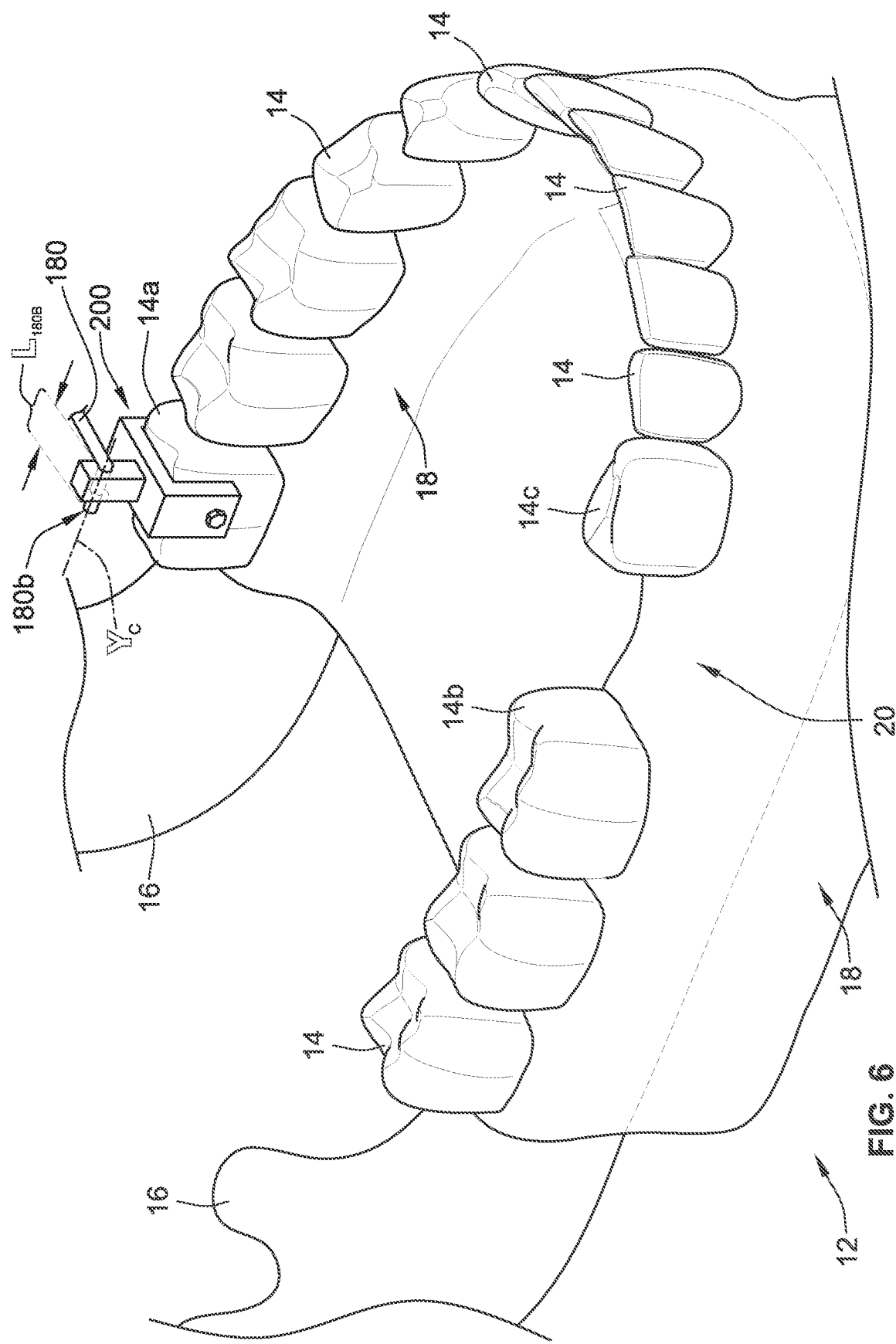
FIG. 6 is a perspective view of the grounding arm of the robotic system of FIG. 1 being coupled with the rigid grounding member that was coupled to the mouth of the patient.

According to some implementations, in order to register the robotic system 100 to the mouth 12 of the patient 10 and establish the origin, O, for use during a procedure using the robotic system 100, the rigid grounding member 200 is installed into the mouth 12 of the patient 10. As shown in FIG. 5, the mouth 12 of the patient 10 includes teeth 14, a jawbone 16, and soft tissue 18 (e.g., gingival tissue), where tooth 14a is selected to be coupled with the rigid grounding member 200. As shown in FIG. 6, the mouth 12 further includes a surgical site 20 (e.g., location to receive a dental implant, permanent abutment, and permanent crown), where teeth 14b and 14c are positioned adjacent to the surgical site 20.

While the rigid grounding member 200 is attached to the tooth 14a, the rigid grounding member 200 can be attached to any of the other teeth 14 in the mouth 12 and/or to the jawbone 16 of the patient 10. To attach the rigid grounding member 200 to the tooth 14a, the rigid grounding member 200 is placed on the tooth 14a. Specifically, for example, the rigid grounding member 200 is positioned in the mouth 12 of the patient 10 such that (i) the bottom surface 209b of the base 209 is positioned generally adjacent to an occlusal surface of the tooth 14a, (ii) the first leg 207a is positioned generally adjacent to a lingual surface of the tooth 14a, and (iii) the second leg 207b is positioned generally adjacent to a buccal surface of the tooth 14a, as shown in FIG. 5. With the rigid grounding member 200 so positioned, the fastener 230 is threaded into the threaded throughbore 208 of the first leg 207a to rigidly lock the rigid grounding member 200 in place against the tooth 14a. In some implementations, the fastener 230 is tightened such that the fastener 230 does not penetrate the tooth 14a, the soft tissue 18, and/or the jawbone 16. However, in some alternative implementations, the fastener 230 does penetrate the tooth 14a, the soft tissue 18, the jawbone 16, or any combination thereof.

With the rigid grounding member 200 attached to the tooth 14a, a scan of the mouth 12 of the patient 10 is taken using a scanner/camera 300 as shown in FIG. 5. Depending on the type of procedure being planned for implementation using the robotic system 100, the scan of the mouth can be an intraoral surface scan using an intraoral scanner, a CT scan using a CT scanner such as, for example, a cone-beam computed tomography (CBCT) scanner also known as a dental CBCT scanner), or a combination thereof. The scanning of the mouth 12 with the rigid grounding member 200 therein, allows for the generation of the pre-operative three-dimensional virtual model 325 (FIG. 1) of the mouth 12 of the patient 10 to be generated. Such a virtual model can be used for developing a surgical plan and/or for designing components to be mated on a dental implant installed in the mouth 12 of the patient 10. Specifically, the virtual model 325 includes a virtual rigid grounding member 200' (FIG. 1) that is used to establish the origin, O, of a coordinate system to be used by the robotic system 100 when conducting a procedure.

After the scanning of the mouth 12, the robotic system 100 is grounded to the mouth 12 of the patient 10. Specifically, the second end 180 of the grounding probe 180 is mated with the rigid grounding member 200 by positioning and/or sliding the second end 180b of the grounding probe 180 into the receiving bore 222 of the coupling post 220 of the rigid grounding member 200. The second end 180b is slid until the locking bearings 182a,b are slid through and outside of the receiving bore 222 and biased outward away from the central axis, $Y_C$, (FIG. 3) such that the grounding probe 180 cannot readily be removed from the receiving bore 222. In some implementations, tactile feedback is used to indicate that the grounding probe 180 is fully engaged with the rigid grounding member 200 and properly positioned therein. For example, when the grounding probe 180 is fully engaged, the locking bearings 182a,b can snap into place making an audible sound and/or a vibrating click.

By readily be removed, it is meant that to remove the grounding probe 180 from its engagement with the rigid grounding member 200, the locking bearings 182a,b need to be actuated by being pressed inward towards the central axis, $Y_C$, to allow the grounding probe 180 to be slid out of the receiving bore 222. Alternatively, the grounding probe 180 can be removed from its engagement with the rigid grounding member 200 by pulling the grounding probe 180 with a sufficient amount of force to overcome the biasing force of the locking bearings 180a,b, thereby causing the locking bearings 182a,b to be forced inward towards the central axis, $Y_C$, and allow the removal of the grounding probe 180 from engagement with the rigid grounding member 200.

As best shown in FIG. 6, a length, $L_{180b}$, of the second end 180b of the grounding probe 180 is designed such that once the grounding probe 180 is properly engaged with the coupling post 220 of the rigid grounding member 200, the grounding probe 180 does not have any or very little translational play therein. That means that the grounding probe 180 cannot slide and/or move laterally (e.g., translation) along the central axis, $Y_C$, when the grounding probe 180 is engaged with the rigid grounding member 200. However, the grounding probe 180 is allowed to rotate within the receiving bore 222 about the central axis, $Y_C$. Such a connection between the grounding probe 180 and the rigid grounding member 200 aids the robotic system 100 in maintaining the known origin, O, based on the location of the rigid grounding member 200 in the mouth 12 of the patient 10.

With the robotic system 100 grounded to the mouth 12 of the patient 10 via the rigid grounding member 200 and the grounding probe 180 (coupled to the grounding arm 160 of the robotic system 100), the robotic system 100 is ready to automatically implement a preplanned procedure and/or to allow an operator 400 to perform a manual and/or a semi-manual procedure that is tracked/traced by the robotic system 100. In the case of using the robotic system 100 to automatically implement/conduct a preplanned procedure, the preplanned procedure must first be planned, for example, using a dental surgical planning software program, as described in the following Section.

Planning a Surgical Plan for Automatic Implementation by the Robotic System 100

As discussed above, the mouth 12 of the patient 10 is scanned with the rigid grounding member 200 therein. The scan data generated from that scan (e.g., intraoral surface scan, CT scan, dental CBCT scan, X-ray scan, a combination thereof, etc.) is imported and/or sent to the computer 121, or another computer, that executes and/or runs a dental surgical planning software program. As shown in FIG. 1, the surgical planning software program is designed to display on the display device 122 the pre-operative three-dimensional virtual model 325 of at least a portion of the mouth 12 of the patient 10. The pre-operative three-dimensional virtual model of the virtual mouth 12' includes virtual teeth 14', virtual soft tissue 18', a virtual surgical site 20', a virtual rigid grounding member 200', and in some implementations where a dental CBCT scan and/or X-ray scan is taken, virtual bone 16' (e.g., jawbone), which correspond with the teeth 14, the soft tissue 18, the surgical site 20, the rigid grounding member 200, and the bone 16 in the actual mouth 12 of the patient 10.

Depending on the type of procedure that is to be conducted in the mouth 12 of the patient 10, the dental surgical planning software program is designed to automatically and/or with some input from an operator (e.g., operator 400 shown in FIG. 7), develop a surgical plan for conducting the desired procedure automatically using one or more of the surgical tool-bits 132 attached to the tool 155 of the working arm 140 of the robotic system 100. Specifically, the dental surgical planning software program is designed to develop a set of instructions and/or movements for the working arm 140 to make relative to the grounding arm 160 (e.g., relative to the second end 180b of the grounding probe 180), which is positioned at a known location relative to the rigid grounding member 200 in the mouth 12 of the patient 10 (e.g., the established origin, O along the central axis, $X_C$, shown in FIG. 4). The developed set of instructions includes directions as to what type and/or size of tool or tools to be used during the surgical procedure. The developed set of instructions also includes an order for using the tools when multiple tools are to be used. For example, if the desired procedure is an osteotomy, the developed instructions include which surgical drill-bit tool or tools 132 to use. Specifically, in an exemplary osteotomy, the instructions may direct the robotic system 100 to first use a first surgical drill-bit tool 132 having a first diameter and a first length to start the procedure e g to create an initial socket/opening in the jawbone), followed by an instruction for the robotic system 100 to switch to a second surgical drill-bit tool 132 having a second (e.g., relatively larger) diameter and a second length (e.g., the same as or different than the first length) to continue the procedure (e.g., to enlarge a diameter of the created socket/opening in the jawbone etc. A subsequent instruction may include for the robotic system 100 to switch to a surgical tapping tool 132 to tap (e.g., create threads) the previously created socket/opening in the jawbone. In some implementations, the surgical system 100 automatically and without operator input switches the surgical tool-bits 132 to the tool 155; and in some alternative implementations, an operator manually attaches and detaches the surgical tool-bits 132 to the tool 155.

The development of the surgical plan by the dental surgical planning software program can be completely autonomous after receipt of the scan data e.g., pre-operative virtual three-dimensional model 325), or the development can involve some input from an operator. For example, the dental surgical planning software program may require an input from the operator such as the type of procedure to be planned (e.g., creation of an osteotomy, implant placement, bone shaving, etc.), the location and orientation for a desired central axis of the implant to be placed (e.g., to avoid a nerve in the mouth 12 and/or to avoid an area of low density bone in the mouth 12), the manufacturer of the implant to be placed, the size of the implant to be placed, etc.

Once the surgical plan is developed using the dental surgical planning software program, the robotic system 100 is ready to conduct/implement the surgical plan using one or more of the surgical tool-bits 132. In some implementations, the computer 121 that controls the working arm 140 and the grounding arm 160 also executes and runs the surgical planning software program. In such implementations, the developed surgical plan is automatically loaded and ready to be automatically implemented by the robotic system 100, for example, in response to an operator clicking a start button on the display device 122. In alternative implementations where a different computer executes/runs the dental surgical planning software program, the developed surgical plan needs to be sent to and/or loaded into the robotic system 100.

Figure 7:
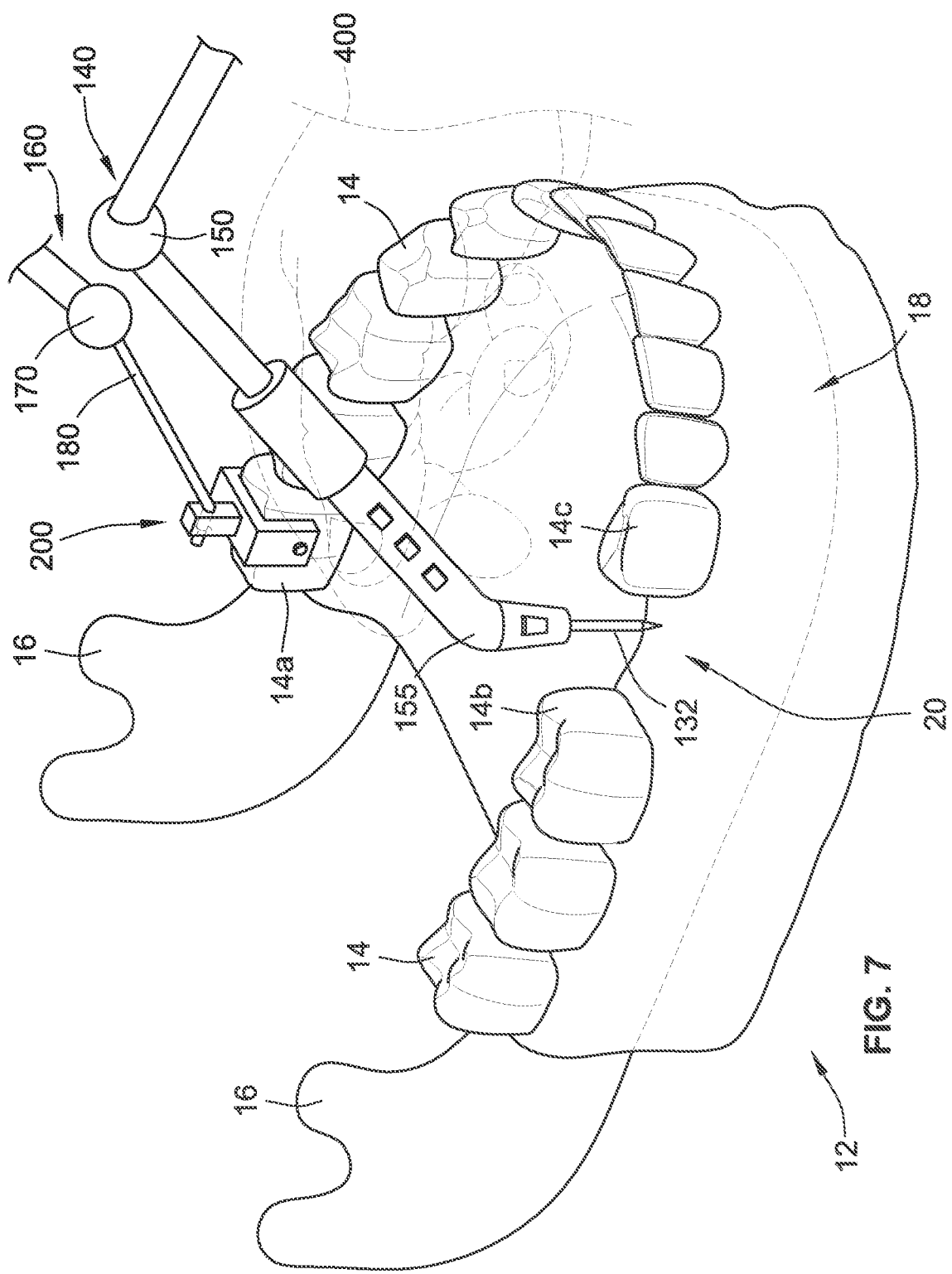
FIG. 7 is a perspective view of the working arm and coupled surgical tool being used to perform a procedure in the mouth of the patient.

As shown in FIG. 7, after the surgical plan is initiated, the working arm 140 moves into place (e.g., at least partially into the mouth 12 of the patient 10) relative to the grounding arm 160 and starts to perform the procedure automatically at the surgical site 20 using one or more of the surgical tool-bits 132.

Defining the Invisible Barrier Wall/Area 450 for Confining Movement of the Robotic System 100

As discussed herein, instead of having the robotic system 100 conduct a surgical procedure automatically, the robotic system 100 can be used manually such that the operator 400 (FIGS. 7, 8A, 8B) causes the working arm 140 and the attached surgical tool-bit 132 to move relative to the patient 10. In such implementations, the invisible barrier wall/area 450 can be established prior to conducting the procedure. As shown in FIG. 8A, the invisible barrier wall/area 450 is shown without the mouth 12 of the patient 10 for illustrative purposes, whereas FIG. 8B illustrates the same invisible barrier wall/area 450 overlaid in the mouth 12 of the patient 10.

The invisible barrier wall/area 450 can be established and/or developed using the surgical planning software program described herein as part of a surgical plan. In such implementations, for a semi-manual procedure to be conducted by an operator using (e.g., manually manipulating) the robotic system 100, the invisible barrier wall/area 450 establishes a boundary for the working arm 140, and specifically the surgical tool-bit 132 coupled thereto, when the surgical tool-bit 132 is near the patient 10 and/or positioned inside of the mouth 12 of the patient 10. As such, the invisible barrier wall/area 450 can aid in preventing the operator (e.g., oral surgeon) from moving the tool 155 in a manner that would cause the surgical tool-bit 132 and/or any portion of the working arm 140 (e.g., including the tool 155) to interfere with the mouth 12 of the patient 10.

By interfere, it is meant, for example, that working arm 140 is bumped into teeth 14 of the patient 10 not being addressed by the procedure being conducted. For another example, by interfere, it is meant that the surgical tool-bit 132 is moved (e.g., vertically up and/or down, side-to-side, etc.) too far into the jawbone 16 of the patient 10 when, for example, the robotic system 100 is being used to perform a semi-manual procedure, such as, for example, creation of an osteotomy. As such, when the operator 400 is manually creating the osteotomy by manually moving the working arm 140, the robotic system 100 implementing the invisible barrier wall/area 450 allows the operator 400 to move the surgical tool-bit 132 as desired (e.g., vertically up and/or down, side-to-side, etc.) within the bounds of the invisible barrier wall/area 450, but if the operator 400 attempts to move the surgical tool-bit 132 outside of and/or past the invisible barrier wall/area 450, then the robotic system 100 actively prevents such a movement using, for example, the motors in the flexible joint members 150. For example, as illustrated in FIGS. 8A and 8B, the operator 400 is attempting to cause the surgical tool-bit 132 to be moved in the direction of arrow A (e.g., downward relative to the orientation of FIG. 8B) through the invisible barrier wall/area 450. However, because the surgical system 100 is actively enforcing the invisible barrier wall/area 450, the surgical system 100 causes the working arm 140, the tool 155, the surgical tool-bit 132, or any combination thereof, to vibrate (e.g., tactile feedback) indicating that the operator is attempting to move the surgical tool 132 past the invisible barrier wall/area 450, which is not allowed. Use of such an invisible barrier wall/area 450 can be used, for example, to allow an operator (e.g., dental surgeon) to perform a free-form-shaped osteotomy where the operator is permitted to sculpt the osteotomy (e.g., move a surgical rotating mill tool 132 vertically up and/or down and side-to-side)—as opposed to using a set of stepped drill bits that are only moved vertically along a single central axis. As such, the operator can in real-time manually modify/update a surgical plan based on the received tactile feedback and/or other information (e.g., a level of torque needed to maintain a desired or preset drill speed during the procedure, a level of force needed to advance the surgical tool-bit 132 during the procedure, etc.).

While the invisible barrier wall/area 450 is shown as having an open top, alternative invisible barrier wall/areas can have invisible walls/invisible surfaces on all sides such that at least a portion of the working arm 140 (e.g., a tip of the surgical tool-bit 132) is completely enclosed within the invisible barrier wall/area during the entire procedure being performed using the robotic system 100. As such, the invisible barrier wall/area can extend outside of the mouth 12 of the patient 10. Such an invisible barrier wall/area can aid in preventing a portion of the working arm 140 from being bumped into the face or head or chest of the patient 10, among other things.

The invisible barrier wall/area 450 is shown in FIGS. 8A and 8B in dashed lines to indicate that the invisible barrier wall/area 450 is not actually visible to the operator of the robotic system 100 in the mouth 12 of the patient 10 during the procedure. However, in some implementations, a virtual representation of the invisible barrier wall/area 450 can be displayed on the display device 122 and/or on another display device during the procedure. For example, a virtual representation of the invisible barrier wall/area 450 can be displayed relative to a virtual model (e.g., the pre-operative three-dimensional virtual model 325) of the mouth 12 of the patient. For another example, a virtual representation of the invisible barrier wall/area 450 can be displayed relative to a live video feed of the mouth 12 of the patient 10. For yet another example, a virtual representation of the invisible barrier wall/area 450 can be displayed relative to a picture of the mouth 12 of the patient 10. The displaying of a virtual representation of the invisible barrier wall/area 450 allows the operator to visualize the invisible barrier wall/area 450 relative to the mouth 12 of the patient 10, which can aid in the operator conducting and/or monitoring/supervising the procedure.

Monitoring/Tracing a Semi-Manual Procedure Using the Robotic System 100

The robotic system 100 can be used to perform a semi-manual procedure. By semi-manual it is meant that the robotic system 100 allows the operator 400 (FIGS. 7, 8A, 8B) of the robotic system 100 to manually manipulate/move the working arm 140 relative to the mouth 12 of the patient 10 to perform a procedure while at the same time maintain a level of control. For example, the robotic system 100 maintains control of the working arm 140 and the grounding arm 160 by supporting its own weight and/or monitoring/sensing the positions of the working arm 140 and the grounding arm 160 relative to the established origin, O (FIG. 8B).

As discussed herein, the working arm 140 includes a multitude of flexible joint members 150 and the grounding arm 160 includes a multitude of flexible joint members 170, where each of the flexible joint members 150, 170 includes one or more sensors for use in determining a position of at least a portion of the working arm 140 (e.g., a tip of the surgical tool-bit 132, etc.) and/or the grounding arm 160 (e.g., a tip of the grounding probe 180). For example, as the operator 400 moves the tool 155 (FIG. 8B), the sensors in the flexible joint members 150, 170 record data that is transmitted to the computer 121 for processing. The computer 121 runs/executes robotic control software that receives the data from the sensors and processes that data to determine a location of at least a portion of the working arm 140 (e.g., a tip of the surgical tool-bit 132) relative to the established origin, O (FIG. 8B).

For example, as shown in FIG. 8B, the origin, O, for the robotic system 100 is established as a central point along the central axis, $X_C$, of the receiving bore 222 of the coupling post 220 and along the central axis, $Y_C$, of the second end 180b of the grounding probe 180. Alternatively, the origin, O, can be established at any location relative to the rigid grounding member 200, as the rigid grounding member 200 is fixed relative to the rest of the mouth 12 of the patient 10 in a known and recorded fashion (e.g., known and recorded during the scanning of the mouth 12 with the rigid grounding member 200 therein as described herein) when installed in the mouth 12.

As the operator 400 conducts a semi-manual procedure, with the robotic system 100 tracking/tracing every movement of the working arm 140 (e.g., specifically tracing every move of a tip of the surgical tool-bit 132) using the sensors in the flexible joint members 150, 170, data about the location of the working arm 140 (and the surgical tool-bit 132) is generated and stored in the computer 121 or another computer and/or memory device. The computer 121 can execute and/or run three-dimensional modeling software (e.g., that is the same as the dental surgical planning software program described elsewhere herein or a different software program) that is programmed to create a modified or post-operative virtual three-dimensional model 326 (FIG. 9) of at least a portion of the mouth 12 of the patient 10. The post-operative virtual three-dimensional model 326 is based on (i) the pre-operative three-dimensional virtual model 325 (FIG. 1) of the mouth 12 and (ii) the data collected regarding the positions of the working arm 140 during the procedure. Specifically, the three-dimensional modeling software is designed to take the pre-operative three-dimensional virtual model 325 of the mouth 12 of the patient 10 and to modify the pre-operative three-dimensional virtual model 325 based on the procedure conducted using the robotic system 100. As such, the post-operative three-dimensional virtual model 326 of the at least a portion of the virtual mouth 12' includes the virtual teeth 14', the virtual soft tissue 18', the virtual surgical site 20', the virtual rigid grounding member 200', and in some implementations that took a CT scan (e.g., a dental CBCT scan), virtual bone 16' (e.g., jawbone), which are in the pre-operative three-dimensional virtual model 325. However, depending on the procedure and the data collected during the same, the post-operative three-dimensional virtual model 326 also includes modifications at the surgical site 20'.

For example, as shown in FIG. 9, if the operator 400 creates an osteotomy using a surgical drill-bit tool 132 while the robotic system 100 tracked the procedure, the tracking of the positions of the working arm 140 produces data indicative of the location of the surgical tool 132 used during the procedure relative to the soft tissue 18 and jawbone 16 in the mouth 12 of the patient 10 relative to the rigid grounding member 200 (and thus the established origin, O). As such, the three-dimensional modeling software is able to identify how the surgical drill-bit tool or tools 132 interfered with the pre-operative three-dimensional virtual model 325 and update the pre-operative three-dimensional virtual model 325 by removing portions thereof based on the interference to result in the post-operative three-dimensional virtual model 326 including a virtual opening or socket 25' in the soft tissue 18' and/or in the bone 16'. That is, the interference of the surgical drill-bit tool or tools 132 indicates that the surgical drill-bit tool or tools 132 were used to drill and/or remove material resulting in the illustrated virtual opening or socket 25'. As such, the three-dimensional modeling software is able to modify the pre-operative three-dimensional virtual model 325 by removing the material that corresponds to the material that was actually removed from the mouth 12 of the patient 10 during the procedure. The result is the modified or post-operative three-dimensional virtual model 326 of the mouth 12 of the patient 10, which depicts the post-operative situation in the mouth 12 of the patient 10 (e.g., with the removed soft tissue and/or jawbone material). Thus, it is not necessary for the operator 400 to take a post-operative scan of the mouth 12 of the patient 10 to acquire the post-operative patient situation. The patient 10 is spared this extra scanning step.

Further, for another example, as shown in FIG. 9, if the operator 400 placed a dental implant using an implant driving tool 132 while the robotic system 100 tracked the procedure, the tracking of the positions of the working arm 140 produces data indicative of the location of the implant driving tool (and thus the position of the dental implant coupled thereto) relative to the rigid grounding member 200 (and thus the established origin, O). As such, the three-dimensional modeling software is able to identify how the implant driving tool (and the dental implant coupled thereto) interfered with and/or moved relative to the pre-operative three-dimensional virtual model 325 and update the pre-operative three-dimensional virtual model 325 based on the interference to result in the post-operative three-dimensional virtual model 326 including a virtual dental implant 30' placed in the virtual opening or socket 25' at a location and orientation that corresponds with the placement and orientation of the actual dental implant installed in the mouth 12 of the patient 10 using the robotic system 100. Thus, it is not necessary for the operator 400 to take a post-operative scan of the mouth 12 of the patient 10 to acquire the post-operative patient situation including the location and orientation of the dental implant installed therein. The patient 10 is spared this extra scanning step.

The tracking/monitoring of the position of the working arm 140 and/or grounding arm 160 during a semi-manual and/or manual procedure conducted using the robotic system 100 can be used to create a variety of modified or post-operative virtual three-dimensional models of at least a portion of the mouth 12 of the patient 10 in addition to the ones described herein and shown in FIG. 9. For example, modified or post-operative virtual three-dimensional models can be automatically generated by, for example, the computer 121 running the three-dimensional modeling software after a conventional dentistry tooth-prep is performed using the robotic system, after a temporary prosthesis is shaped using the robotic system 100, after a denture is modified using the robotic system 100, etc. Various other manual/semi-manual procedures, such as the procedures described elsewhere herein, can be tracked/monitored as described above for generating positional data for use in generating modified or post-operative virtual three-dimensional models, thereby avoiding post-operative scans (e.g., post-operative intraoral surface scans, post-operative dental CBCT scan, etc.).

Exemplary uses of the Robotic System 100

The robotic system 100 of the present disclosure can be used to conduct a variety of procedures automatically, manually, or a combination thereof. One example of a procedure performable by the robotic system 100 is the creating of an osteotomy. The creating of the osteotomy is performed using one or more surgical drill-bit tools 132 coupled to the robotic system 100 to form a socket and/or opening in a jawbone 16 of a patient 10 that is suitable for receiving a dental implant therein. Additionally, in some implementations, the performing of the osteotomy also uses one or more surgical tapping tools 132 coupled to the robotic system 100 to form threads in the previously formed socket/opening in the jawbone 16 of the patient 10 that is suitable for receiving the dental implant therein. A second example of a procedure performable by the robotic system 100 is the installing of a dental implant. The installing of the dental implant is performed using an implant driving tool 132 coupled to the robotic system 100 to install the dental implant in an opening in a jawbone 16 of a patient 10. A third example of a procedure performable by the robotic system 100 is the performing of an alveolectomy. The alveolectomy is performed using a bone shaving/removal tool 132 coupled to the robotic system 100 to removal bone material from a jawbone 16 of a patient 10. A fourth example of a procedure performable by the robotic system 100 is the performing of an alveoloplasty. The alveoloplasty is performed using a surgical bone contouring tool 132 coupled to the robotic system 100 to contour a portion of a jawbone 16 of a patient 10. A filth example of a procedure performable by the robotic system 100 is the developing of a tooth-crown-prep. The development of a tooth-crown-prep is performed using one or more surgical dental drill-bit tools 132 and/or dental shaver tool-bits 132 to remove portions of a tooth (e.g., occlusal portions) such that the tooth is suitable for receiving a custom crown thereon. A sixth example of a procedure performable by the robotic system 100 is the modifying of a denture for use as part of a hybrid prosthesis. A hybrid prosthesis includes a modified denture bonded with one or more abutments or cylinders. Typically, the modified denture is coupled to the dental implants via the one or more abutments or cylinders, which attach to respective ones of the dental implants. The robotic system 100 can be used to aid in the creation of the modified denture by precisely drilling holes in the denture in locations that directly correspond with central axes of the dental implants installed in the mouth of a patient 10, which were installed using the robotic system 100. As such, when the one or more abutments or cylinders are attached to the dental implants, the drilled holes in the denture match up with (i.e., are aligned with) the abutments or cylinders and can be bonded thereto to create the hybrid prosthesis. A seventh example of a procedure performable by the robotic system 100 is the creating of a provisional restoration. The creating of the provisional restoration is performed using one or more shaver and/or sculpting tool-bits 132 to remove portions of a tooth blank such that the tooth blank is sculpted to have an anatomical tooth shape for attachment to an installed dental implant.

It is contemplated that any of the above seven examples and any of the following disclosed implementations, can be performed automatically by the robotic system 100 loaded with a surgical plan with no or little input from an operator (e.g., except for selecting of a start procedure button), or performed manually and/or semi-manually by an operator 400 that manually manipulates the working arm 140 of the robotic system 100 that is either constrained by or free from an invisible barrier wall/area 450. It is further contemplated that any element and/or step from any of the following implementations can be removed and/or replaced with any other disclosed element in any of the other disclosed implementations.

According to a first implementation of the disclosed concepts of the present disclosure, the robotic system 100 is used to install a dental implant in the mouth 12 of the patient 10. The robotic system 100 includes the base 120, the grounding arm 160, the working arm 140, and one or more sensors. The grounding arm 160 has a first end 161a and a second end 161b, The first end 161a of the grounding arm 160 is coupled to the base 120 and the second end 161b of the grounding arm 160 is configured to be coupled to a fixed structure in the mouth 12 of the patient 10 for establishing the origin, O, for the robotic system 100 relative to the mouth 12 of the patient 10. In such implementations, the second end 161b of the grounding arm 160 has at least six degrees of freedom relative to the base 120. The working arm 140 has a first end 141a and a second end 141b. The first end 141a of the working arm 140 extends from the base 120 and the second end 141b of the working arm 140 is configured to be coupled with one or more of the surgical tools 132 for use during installation of the dental implant in the mouth 12 of the patient 10. A portion of the working arm 140 has at least six degrees of freedom relative to the base 120 and is movable to (i) form an opening in the bone 16 within the mouth 12 of the patient 10 and (ii) install the dental implant in the formed opening. The one or more sensors (e.g., the sensors in the flexible joint members 150, 170) monitor the positions of the grounding arm 160 and the working arm 140 and generate positional data that is used to create a post-operative virtual three-dimensional implant level model (e.g., model 326 of FIG. 9) of at least a portion of the mouth 12 of the patient 10.

In the first implementation, the post-operative virtual three-dimensional implant level model is created without use of a scanning abutment coupled to the dental implant installed in the mouth 12 of the patient 10. Further, the movable portion of the working arm 140 is (i) manually-movable by the operator 400 of the robotic system 100, (ii) automatically movable by one or more motors (e.g., motors in the flexible joint members 150, 170) of the robotic system 100, or (iii) both. The fixed structure in the mouth 12 of the patient 10 is one or more teeth, jawbone, the rigid grounding member 200, or any combination thereof.

According to a second implementation of the disclosed concepts of the present disclosure, a method of creating the post-operative virtual three-dimensional model 326 (FIG. 9)

of at least a portion of the mouth 12 of the patient 10, where the mouth 12 includes a dental implant installed using the robotic system 100 during a dental surgical procedure, includes attaching the rigid grounding member 200 to a fixed position within the mouth 12 of the patient 10. The method also includes obtaining the pre-operative virtual three-dimensional model 325 (FIG. 1) of the mouth 12 of the patient 10 with the rigid grounding member 200 therein. The method further includes, coupling the grounding arm 160 of the robotic system 100 to the rigid grounding member 200 in the mouth 12 of the patient 10, thereby establishing the origin, O, (FIG. 8B) for the mouth 12 of the patient 10. The method also includes moving (e.g., automatically or manually, or a combination of both), as part of the dental surgical procedure, at least a portion of the working arm 140 of the robotic system 100 coupled to the dental-implant-driving tool 132 to install the dental implant in the mouth 12 of the patient 10. The method also includes monitoring, during the dental surgical procedure, a position of the grounding arm 160 and the working arm 140 to generate positional data related to the location of the dental-implant-driving tool 132 relative to the established origin, O and creating the post-operative virtual three-dimensional model 326 (FIG. 9) of the at least a portion of the mouth 12 of the patient 10 based on the obtained pre-operative virtual three-dimensional model 325 (FIG. 1) and the generated positional data.

In the second implementation, the creating the post-operative virtual three-dimensional model 326 (FIG. 9) occurs without use of a scanning abutment coupled to the installed dental implant. Further, the creating includes modifying the pre-operative virtual three-dimensional model 325 of the mouth 12 of the patient 10 to include at least a portion of a virtual model of the dental implant (e.g., virtual dental implant 30' shown in FIG. 9) installed in the mouth 12 of the patient 10. In some versions of the second implementation, the method further includes prior to the moving, determining the invisible boundary wall/area 450 (FIGS. 8A and 8B) to be established around a pre-determined location (e.g., the surgical site 20 shown in FIGS. 6 and 7) for the dental implant to be installed in the mouth 12 of the patient 10 and during the moving, automatically enforcing the determined invisible boundary wall/area 450 by preventing the working arm 140 of the robotic system 100 from being moved in a manner that would cause the dental implant to be installed outside of the determined invisible boundary wall/area 450.

According to a third implementation of the disclosed concepts of the present disclosure, a method of automatically shaving alveolar bone in the mouth 12 of the patient using the robotic system 100 includes attaching the rigid grounding member 200 to a fixed position (e.g., tooth 14a shown in FIG. 6) within the mouth 12 of the patient 10. The method further includes obtaining a pre-shaved virtual model (e.g., the same as, or similar to, the pre-operative three-dimensional virtual model 325 shown in FIG. 1) of the mouth 12 of the patient 10 with the rigid grounding member 200 therein. The method further includes coupling the grounding arm 160 of the robotic system 100 to the rigid grounding member 200 in the mouth 12 of the patient 10, thereby establishing the origin, O, (FIG. 8B) for the mouth 12 of the patient 10. The method further includes developing a plan for automatically moving a bone-cutting tool 132 relative to the established origin, O, to shave a portion of the alveolar bone in the mouth 12 of the patient 10. The method further includes attaching the bone-cutting tool 132 to the working arm 140 of the robotic system 100 and executing the developed plan by automatically moving the bone-cutting tool 132 via the working arm 140 of the robotic system 100, thereby shaving the alveolar bone in the mouth 12 of the patient 10 according to the developed plan such that an exposed ridge of the alveolar bone in the mouth 12 of the patient 10 is sufficiently widened for drilling and receiving a dental implant therein.

According to a fourth implementation of the disclosed concepts of the present disclosure, a method of installing a dental implant in the mouth 12 of the patient 10 using the robotic system 100 includes developing a plan for installing the dental implant in the mouth 12 of the patient 10. The developed plan includes (i) a first sub-plan for shaving an exposed portion of bone in the mouth 12 with a first tool 132 (e.g., a surgical bone shaver), thereby creating a sufficiently widened portion of the bone for receiving the dental implant therein, (ii) a second sub-plan for forming an opening or socket in the sufficiently widened portion of the bone to receive the dental implant with a second tool 132 (e.g., a surgical drill-bit tool), and (iii) a third sub-plan for installing the dental implant within the opening with a third tool 132 (e.g., an implant driving tool). The method further includes establishing the origin, O, (FIG. 8B) for the mouth 12 of the patient 10 by coupling the grounding arm 160 of the robotic system 100 to the rigid grounding member 200 in the mouth 12 of the patient 10. Then the plan is executed by (1) coupling the first tool 132 to the working arm 140 of the robotic system 100 and shaving the exposed portion of the bone in the mouth 12 of the patient 10 by moving at least a portion of the working arm 140 (e.g., by moving the tool 155 shown in FIG. 2) according to the first sub-plan, (2) coupling the second tool 132 to the working arm 140 of the robotic system 100 and forming the opening in the bone 16 (FIG. 7) in the mouth 12 of the patient 10 by moving the at least a portion of the working arm 140 according to the second sub-plan, and (3) coupling the third tool 132 and the dental implant to the working arm 140 of the robotic system 100 and installing the dental implant into the opening in the bone 16 in the mouth 12 of the patient 10 by moving the at least a portion of the working arm 140 according to the third sub-plan.

In the fourth implementation, the method can further include monitoring, during the installing the dental implant, a position of the grounding arm 160 and the working arm 140 to generate positional data related to (1) the location of the dental implant relative to the established origin, O, (ii) the location of the third tool 132 relative to the established origin, O, or (iii) both (i) and (ii). Further, the method can further include creating a post-operative virtual three-dimensional model (e.g., the same as, or similar to, the modified or post-operative virtual three-dimensional model 326 shown in FIG. 9) of at least a portion of the mouth 12 of the patient 10 based on the obtained pre-operative virtual model 325 and the generated positional data, where the at least a portion of the mouth 12 includes the dental implant. In the fourth implementation, the creating the post-operative virtual three-dimensional model occurs without use of a scanning abutment coupled to the installed dental implant.

According to a fifth implementation of the disclosed concepts of the present disclosure, a method of shaving alveolar bone in the mouth 12 of the patient 10 using the robotic system 100 includes establishing the origin, O, (FIG. 8B) for the mouth 12 of the patient 10 by coupling the grounding arm 160 of the robotic system 100 to the rigid grounding member 200 in the mouth 12 of the patient 10. The method further includes determining the invisible boundary wall/area 450 to be established around a pre-determined location (e.g., the surgical site 20 shown in FIGS. 6 and 7) in the mouth 12 of the patient 10. The method further includes coupling a bone-cutting tool 132 to the working arm 140 of the robotic system 100 and moving (e.g., manually moving) at least a portion of the working arm 140 of the robotic system 100 to shave the alveolar bone in the mouth 12 of the patient 10. During the moving, the method further includes automatically enforcing the determined invisible boundary wall/area 450 by preventing the working arm 140 of the robotic system 100 from being moved in a manner that would cause the bone-cutting tool 132 to be moved past the determined invisible boundary wall/area 450. The method further includes monitoring, during the moving, a position of the grounding arm 160 and/or the working arm 140 to generate positional data related to the location of the bone-cutting tool 132 relative to the established origin, O.

According to a sixth implementation of e disclosed concepts of the present disclosure, a method of automatically preparing a tooth in the mouth 12 of the patient 10 to receive a custom crown using the robotic system 100 includes attaching the rigid grounding member 200 to a fixed position (e.g., tooth 14a shown in FIG. 5) within the mouth 12 of the patient 10 and obtaining a pre-shaped virtual three-dimensional model (e.g., the same as, or similar to, the pre-operative three-dimensional virtual model 325) of the mouth 12 of the patient 10 with the rigid grounding member 200. The method further includes coupling the grounding arm 160 of the robotic system 100 to the rigid grounding member 200 in the mouth 12 of the patient 10, thereby establishing the origin, O, (FIG. 8B) for the mouth 12 of the patient 10. The method further includes developing a plan for automatically moving one or more tools 132 relative to the established origin, O, to shape the tooth in the mouth 12 of the patient 10 to receive the custom crown. In response to the working arm 140 of the robotic system 100 being coupled with at least one of the one or more tools 132, the method further includes implementing the developed plan by automatically moving at least a portion of the working arm 140 (e.g., the tool 155 best shown in FIG. 2) according to the developed plan, thereby shaping the tooth in the mouth 12 of the patient 10 such that the tooth is substantially shaped according to the developed plan.

In the sixth implementation, the method can further include designing the custom crown based on the developed plan, fabricating the designed custom crown using a fabrication machine, and attaching the fabricated custom crown to the prepared tooth.

According to a seventh implementation of the disclosed concepts of the present disclosure, a method of preparing a tooth in the mouth 12 of the patient 10 to receive a custom crown using the robotic system 100 includes attaching the rigid grounding member 200 to a fixed position (e.g., tooth 14a shown in FIG. 5) within the mouth 12 of the patient 10 and obtaining a pre-shaped virtual three-dimensional model (e.g., the same as, or similar to, the pre-operative three-dimensional virtual model 325) of the mouth 12 of the patient 10 with the rigid grounding member 200 therein. The method further includes determining the invisible boundary wall/area 450 to be established around the tooth in the mouth 12 to be shaped. The method further includes coupling the grounding arm 160 of the robotic system 100 to the rigid grounding member 200 in the mouth 12 of the patient 10, thereby establishing the origin, O, for the mouth 12 of the patient 10. In response to the working arm 140 of the robotic system 100 being coupled with a shaping tool 132, the method further includes manually moving at least a portion of the working arm 140 (e.g., the tool 155 best shown in FIG. 2) to shape the tooth in the mouth 12 of the patient 10. The method further includes automatically enforcing the determined invisible boundary wall/area 450 by preventing the working arm 140 from being moved in a manner that would cause a cutting portion of the shaping tool 132 to move outside of the determined invisible boundary wall/area 450. The method further includes monitoring, during the moving, a position of the grounding arm 160 and/or the working arm 140 to generate positional data related to the location of the cutting portion of the shaping tool 132 relative to the established origin, O. The method further includes creating a post-shaped virtual three-dimensional model (e.g., similar to the post-operative virtual three-dimensional model 326 shown in FIG. 9) of at least a portion of the mouth 12 of the patient 10 based on the obtained pre-shaped virtual model and the generated positional data, wherein the at least a portion of the mouth 12 includes the shaped tooth.

In the seventh implementation, the creating the post-shaped virtual model occurs without scanning the mouth after the manually moving. Further, the determined invisible boundary wall/area 450 allows for the manual moving of the at least a portion of the working arm 140 to shape the tooth while maintaining a convergent axial wall angulation of the tooth and allowing manual up and down movements along a long axis of the tooth to allow creation of a crown margin that follows a gingival margin contour in the mouth 12 of the patient 10. Further, the pre-shaped virtual three-dimensional model can be derived from scan data generated during a CT scan, scan data generated during an intraoral surface scan, scan data generated during a surface scan of an impression of at least a portion of the mouth of the patient, scan data generated during a surface scan of a physical model of at least a portion of the mouth 12 of the patient 10, or any combination thereof.

According to an eighth implementation of the disclosed concepts of the present disclosure, a method of modifying a denture to be coupled with a plurality of dental implants in the mouth 12 of the patient 10 (e.g., via abutments or cylinders bonded to the modified denture) as a hybrid prosthesis using the robotic system 100 includes obtaining a first virtual model of the mouth 12 of the patient 10 with the denture therein. The method further includes removing the denture from the mouth 12 of the patient 10 and attaching a first rigid grounding member (e.g., the rigid grounding member 200) to a fixed position (e.g., the tooth 14c shown in FIG. 5) within the mouth 12 of the patient 10. The method further includes obtaining a second virtual model of the mouth 12 of the patient 10 with the first rigid grounding member therein and attaching a second rigid grounding member to the denture outside of the mouth 12 of the patient 10. The method further includes obtaining a third virtual model of the denture with the second rigid grounding member attached thereto. The method further includes establishing the origin, O, (FIG. 8B) for the mouth 12 of the patient 10 by coupling the grounding arm 160 of the robotic system 100 to the first rigid grounding member (e.g., the rigid grounding member 200) in the mouth 12 of the patient 10. The method further includes using the working arm 140 of the robotic system 100 coupled to a dental-implant-driving tool 132 to install the plurality of dental implants in the mouth 12 of the patient 10 and monitoring, during the installing, a position of the grounding arm 160 and/or the working arm 140 to generate positional data related to the location of the dental-implant-driving tool 132 relative to the established origin, O. The method further includes creating a fourth virtual model of at least a portion of the mouth 12 of the patient 10 based on the obtained second virtual model and the generated positional data. Based at least in part on the first, the third, and the fourth virtual models, the method includes developing a plan for automatically modifying the denture such that the denture can be coupled with the installed plurality of dental implants (e.g., via a plurality of abutments or cylinders bonded to the modified denture that mate with the installed dental implants). The method further includes coupling the grounding arm 160 of the robotic system 100 to the second rigid grounding member attached to the denture. The method further includes using the working arm 140 of the robotic system 100, coupled to a drill-bit tool 132, to modify the denture by creating a plurality of holes therein. The holes are created in the denture at specific positions such that abutments or cylinders attached to the dental implants align with the holes such that the modified denture can be bonded to the abutments or cylinders and form the hybrid prosthesis. Additional details on hybrid prostheses, dentures, and the modification of dentures to be used in/as a hybrid prosthesis can be found in U.S. Published Patent Application No. 2014-0272797, which is hereby incorporated by reference herein in its entirety.

According to a ninth implementation of the disclosed concepts of the present disclosure, a method of manufacturing a patient specific temporary prosthesis (PSTP) for use in manufacturing a permanent prosthesis for attachment to a dental implant installed in a mouth of a patient includes establishing an origin for a PSTP blank by coupling the grounding arm 160 of the robotic system TOO to the PSTP blank via a fixture. The method further includes using the working arm 140 of the robotic system 100 coupled to a sculpting tool 132 to modify the PSTP blank such that the PSTP blank is transformed into the PSTP having a tooth-like shape suitable for attachment to the dental implant installed in the mouth 12 of the patient 10. The method further includes monitoring, during the modifying, a position of the grounding arm 160 and/or the working arm 140 to generate positional data related to the location of the sculpting tool 132 relative to the established origin. Based at least in part on the generated positional data, the method further includes creating a virtual three-dimensional model of at least a portion of the PSTP and attaching the PSTP to the dental implant in the mouth 12 of the patient 10. The method further includes permitting gingival tissue (e.g., soft tissue 18 shown in FIGS. 6 and 7) surrounding the PSTP to heal in the mouth 12 of the patient 10. In response to the healed gingival tissue surrounding the PSTP in the mouth 12 of the patient 10 satisfying a threshold, the method further include manufacturing the permanent prosthesis as a replica of the PSTP using the created virtual model. However, in response to the healed gingival tissue surrounding the PSTP in the mouth 12 of the patient 10 not satisfying the threshold, the method further includes (i) physically modifying the PSTP, (ii) scanning the modified PSTP to obtain a modified virtual model of at least a portion of the modified PSTP, and (iii) manufacturing the permanent prosthesis as a replica of the modified PSTP using the obtained modified virtual model. Additional details on PSTPs, fixtures, and the use of PSTPs for creating and/or designing permanent components can be found in U.S. Published Patent Application Nos. 2014-0080095 and 2014-0080092, which are both hereby incorporated by reference herein in their entireties.

According to a tenth implementation of the disclosed concepts of the present disclosure, the robotic system 100 is used to section (e.g., remove and/or cut) soft tissue (e.g., gingival tissue) in the mouth 12 of the patient 10. The sectioning involves the coupling of a cutting tool 132 (e.g., scalpel tool) to the working arm 140 of the robotic system 100. Using the robotic system to automatically section the soft tissue 18 can be result in soft tissue modification that is more predictable and/or more reliable than free-handing an incision using, for example, a tissue punch or a freehand scalpel. Further, the use of the robotic system 100 coupled to a scalpel tool 132 to section soft tissue can result in accelerated and/or more aesthetic healing of the soft tissue as compared to free-handing an incision. In some implementations, the soft tissue can be carved out using the robotic system 100 to create a location to place a dental implant. In some implementations, soft tissue can be carved out using the robotic system 100 for use in other areas in the mouth (e.g., for use in a tissue graft).

According to an eleventh implementation of the disclosed concepts of the present disclosure, after registering the robotic system 100 to a mouth of a patient using a rigid grounding member as described herein, the robotic system 100 is used to track the location of drilled sockets/openings (e.g., during the creation of an osteotomy) in the jawbone 16 (FIG. 5) that are then filled with idealized bone grafting materials. The grafting materials are allowed to osseointegrate with the jawbone material and the patient is allowed to heal (e.g., for six months). After a sufficient amount of healing has occurred, the patient can return for the installation of dental implants at the locations of the grafting materials. The robotic system 100 is then reregistered to the mouth of the patient by, for example, reattaching a rigid grounding member to the mouth of the patient in the same exact location as previously installed. Alternatively, the rigid grounding member is left in the mouth of the patient during the healing phase. In such an alternative implementation, the rigid grounding member may have a size and shape such that the rigid grounding member does not interfere with the patient's mastication function. For example, such a rigid grounding member may be a surgical screw that partially protrudes from a jawbone of the patient in a manner that does not significantly impact the patient's mastication functions. As the robotic system 100 was used to create the sockets/openings that were filled with the grafting materials, the robotic system 100 knows the locations of the idealized bone grafting materials (e.g., by tracking the movements of the working arm 140 during the original drilling relative to an established origin in the mouth of the patient) and can be preprogrammed to automatically drill the location of the idealized bone grafting materials to place the dental implants therein. As it is desirable to install the dental implants into the idealized bone graft materials and not the relatively soft jawbone material therearound, this eleventh implementation aids the operator in placement of the dental implants without having to take a CT scan of the mouth of the patient after the bone grafts are performed.

Portions of the present disclosure describe that a post-operative virtual model of a portion of a mouth of a patient can be created without taking a post-operative scan of the mouth of the patient. However, in some alternative implementations, a post-operative intraoral surface scan can be taken without a scan member (e.g., scannable healing abutment, scan cap, etc.) attached to an installed implant to capture soil tissue information. This surface scan can be merged with a pre-operative CT scan of the mouth of the patient as modified by data Obtained the tracing of the procedure as described herein to create a post-operative virtual model. That is, the post-operative virtual models described herein can further be modified by merging with a port-operative intraoral surface scan to, for example, improve the accuracy of the soft tissue in the post-operative virtual model. Additional details on creating a virtual model with bone/hard tissue information and soft tissue information can be found in U.S. Pat. No. 8,651,858, which is hereby incorporated by reference herein in its entirety.

Portions of the present disclosure describe using the robotic system 100 to shave or sculpt portions of a jawbone 16 in the mouth 12 of the patient 10. It is important to note that such sculpting occurs in three dimensions as the bone can be removed in an X-Y plane and/or in the Z-axis direction. A non-limiting example of when bone may be removed is to remove a narrow ridge of bone where it is desired to place a dental implant. The removing of such bone will result in a wider ridge (e.g., an adequate amount of restorative space) that is better for drilling to receive the dental implant as compared to a narrow ridge. Further, the shaving or sculpting of bone can be used to manipulate a vertical dimension of occlusion (VDO) in the mouth 12 of the patient 10 to provide an adequate amount of restorative space in light of the stack up height of the designed/desired restorative components e.g., dental implant, abutment, crown, etc.) that will be installed in the mouth of the patient. Thus, in some implementations, the robotic system 100 is used to shave bone (e.g., alveolar ridge bon such that the VDO is manipulated such that the installed components (e.g., dental implant, abutment, crown, etc.) fit properly within the mouth 12 of the patient 10. Specifically, such that the occlusal surface of the installed crown mates with the occlusal surface of the opposing tooth/teeth in the mouth 12 of the patient 10.

Portions of the present disclosure describe various surgical tools 132. In addition to the described tools 132, various other tools 132 can be coupled with the working arm 140 of the robotic system 100 and used in the same, or similar, fashion as described herein. For example, a probe tool 132 (e.g., a tool with a metal ball or hook) can be coupled to the working arm 140 for use in checking for pockets between teeth and gingival tissue. The robotic system 100 can use the probe tool 132 to determine a length and/or depth of such pockets. Further, the probe tool 132 can be used as a mechanical sensing probe to find the location of structures (e.g., the rigid grounding member 200, teeth, gingival tissue, palate, etc.) in the mouth 12 of the patient 10. Such a use of the robotic system 100 can be used when, for example, an oral surgeon performs a manual procedure without using the working arm 140 of the robotic system 100 and then wants to use the robotic system 100 to digitally capture any modifications made to the mouth 12 of the patient 10. In such a scenario, the operator (e.g., oral surgeon) can use the robotic system 100 with a mechanical sensing probe coupled to the working arm 140 to sense any changes in the mouth 12. Further, the mechanical sensing can be used to deter hard structures in the mouth 12 like teeth and bone and/or the mechanical sensing can be used to determine soft tissue contours and/or depths of soft tissue at a particular site.

Portions of the present disclosure describe using the robotic system 100 to create an osteotomy in the jawbone 16 of the patient 10. It is important to note that the surgical plan implemented by the robotic system 100 to perform an osteotomy procedure is based, at least in part, on information regarding the quality (e.g., density) of the jawbone 16 in the patient 10 at the surgical site 20, which is typically derived from a CT scan (e.g., a dental CBCT scan) and/or an X-ray scan. This determination can be performed automatically by the dental surgical planning software program and/or manually by an operator and inputted into the dental surgical planning software program. The bone quality at a surgical site 20 is typically categorized as one or more of four types of bone including Type I, Type II, Type III, or Type IV bone, where Type I is the most dense and Type IV is the least dense. Thus, in a patient 10 determined to need a dental implant in a surgical site 20 having Type I bone, the surgical plan may include instructions for the robotic system 100 to create a right-size socket/opening in the jawbone 16 and then to tap the socket/opening with a surgical tapping tool 132. By right-size socket/opening it is meant that the diameter of the created socket/opening and/or of the final drill-bit tool 132 used to create the osteotomy is about equal to a minor diameter of the dental implant to be installed therein. For another example, in a patient 10 determined to need a dental implant in a surgical site 20 having Type IV bone, the surgical plan may include instructions for the robotic system 100 to create an under-size socket/opening in the jawbone 116 without tapping the socket/opening. By under-size socket/opening it is meant that the diameter of the created socket/opening and/or of the final drill-bit tool 132 used to create the osteotomy is smaller than a minor diameter of the dental implant to be installed therein.

In some implementations, the robotic system 100 includes one or more sensors that generate data during the performance of a desired procedure (e.g., osteotomy) that is used in modifying/updating the surgical plan in real-time (e.g., after the procedure is already underway—has already started to be implemented). The sensors can include the sensors described elsewhere herein (e.g., the sensors in the flexible joint member 150 coupled to the rigid arm members 145), one or more torque sensors coupled to the tool 155, one or more force sensors coupled to the tool 155, one or more speed sensors coupled to the tool 155, etc. When performing a surgical plan for an osteotomy, the robotic system 100 initially uses a first surgical drill-bit tool 132 having a first diameter to start the socket/opening in the jawbone 16. The robotic system 100, as it drills the jawbone 16 with the first surgical drill-bit tool 132, monitors the data generated by the sensors to determine if the jawbone 16 is more or less dense than initially determined. Based on the data and/or the determination during the procedure (e.g., during the drilling using the first surgical drill-bit tool 132), the surgical plan can be automatically modified/updated in real-time by the robotic system 100 and/or an operator can be prompted to permit a suggested modification. For example, if the robotic system 100 determines that the data from the sensors (e.g., torque sensors, force sensors, etc.) indicates that the required torque to spin the first surgical drill-bit tool 132 at the planned rate (e.g., 2000 RPMs) and/or the required force to advance the first surgical drill-bit tool 132 into the jawbone 16 is less than anticipated (e.g., based on the previously determined Type I bone), the robotic system 100 may alter or propose to alter the surgical plan because the actual dental situation appears to be different than initially determined. That is, the required less than anticipated torque/force indicates that the jawbone 16 being drilled is not Type I bone, but rather, type II bone. In such a situation, the surgical plan can be changed by, for example, not tapping the created socket/opening and/or by changing the final surgical drill-bit tool 132 to create an under-sized socket/opening as opposed to a right-sized socket/opening as originally planned for the Type I jawbone. The modification of the surgical plan can also include a change in the number of stepped surgical drill-bit tools 132 used in the creation of the osteotomy. For example, if the original surgical plan instructions called for three separate stepped surgical drill-bit tools 1132 to be used for drilling Type IV bone, and during the procedure the robotic system 100 determines that the patient actually has Type II bone (e.g., based on the data from the torque and force sensors, etc.), the surgical system 100 can automatically on the fly in real-time modify/update the surgical plan to add a fourth intermediate surgical drill-bit tool 132. Various other modifications can be made to the surgical plan based on the monitored data from the torque and force sensors and/or other sensors. In summary, the robotic system 100 can modify/update a preplanned surgical plan based on real-time data with or without operator input. Examples of such modifications include (1) changing a preplanned amount of torque (e.g., applied to a surgical drill-bit tool, a surgical tapping tool, etc.) to be used by the robotic system when executing the developed plan; (2) changing a preplanned rotational speed (e.g., applied to a surgical drill-bit tool, a surgical tapping tool, etc.) to be used by the robotic system when executing the developed plan; (3) changing a preplanned amount of force (e.g., applied to a surgical drill-bit tool, a surgical tapping tool, etc.) to be used by the robotic system when executing the developed plan; (4) changing a preplanned number of the plurality of surgical tools (e.g., four surgical drill-bit tools instead of two surgical drill-bit tools) to be used by the robotic system when executing the developed plan. Such modifications are intended to increase the relative initial stability (e.g., resistance to motion from mastication forces) in installed dental implants, and this may promote increased reliability and overall survivability for the dental implants and the implant-borne prostheses.

While the present disclosure has been described with reference to one or more particular embodiments and implementations, those skilled in the art will recognize that many changes may be made thereto without departing from the spirit and scope of the present disclosure. Each of these embodiments and implementations and obvious variations thereof is contemplated as falling within the spirit and scope of the present invention, which is set forth in the claims that follow.

What is claimed is:

1. A robotic system for use during a dental surgical procedure including installation of a dental implant in a mouth of a patient, the robotic system comprising:
a base;
a grounding arm having a first end and a second end, the first end of the grounding arm being coupled to the base, the second end of the grounding arm being configured to be coupled to a fixed structure within the mouth of the patient for establishing an origin for the robotic system relative to the mouth of the patient, the second end of the grounding arm having at least six degrees of freedom relative to the base;
a working arm having a first end and a second end, the first end of the working arm extending from the base, the second end of the working arm being configured to be coupled with one or more tools for use during the dental surgical procedure, a portion of the working arm having at least six degrees of freedom relative to the base and being moveable to (i) form an opening in bone within the mouth of the patient and (ii) install the dental implant in the formed opening; and
one or more sensors to monitor positions of the grounding arm and the working arm relative to the origin, the one or more sensors generating positional data that is used to create a post-operative virtual three-dimensional implant level model of at least a portion of the mouth of the patient, the post-operative virtual model including a virtual dental implant that corresponds to a location and orientation of the dental implant in the mouth of the patient, and the post-operative virtual model is created without scanning.

2. The robotic system of claim 1, wherein the post-operative virtual three-dimensional implant level model is created without use of a scanning abutment coupled to the dental implant installed in the mouth of the patient.

3. The robotic system of claim 1, wherein the generated positional data is used to modify a pre-operative virtual model of the mouth of the patient to include at least a portion of a virtual three-dimensional model of the dental implant installed in the mouth of the patient during the dental surgical procedure.

4. The robotic system of claim 1, wherein the one or more tools include a drill-bit tool, a dental-implant-driving tool, a rotating mill tool, a saw tool, a probe tool, a scalpel tool, or any combination thereof.

5. The robotic system of claim 1, wherein the one or more sensors are electrically coupled to one or more processors of the robotic system and physically mounted to the grounding arm, the working arm, or both.

6. The robotic system of claim 1, wherein the moveable portion of the working arm is (i) manually-movable by an operator of the robotic system, (ii) automatically moveable by one or more motors of the robotic system, or (iii) both.

7. The robotic system of claim 1, wherein the fixed structure within the mouth of the patient is one or more teeth, jaw bone, or both.

8. A robotic system for use during installation of a dental implant in a mouth of a patient, the robotic system comprising:
a base;
a grounding arm extending from the base and being configured to be coupled to a fixed structure within the mouth of the patient for establishing an origin for the robotic system relative to the mouth of the patient;
a working arm extending from the base and being configured to be coupled with one or more tools for use during the installation of the dental implant, at least a portion of the working arm being movable to install the dental implant in the mouth of the patient; and
one or more sensors to monitor positions of the grounding arm and the working arm, the one or more sensors generating positional data related to the location of the one or more tools relative to the established origin, wherein a post-virtual model of at least a portion of the mouth of the patient is created based on a pre-operative virtual model of the at least the portion of the mouth of the patient and the generated positional data, the post-virtual model including a virtual dental implant that corresponds to a location and orientation of the dental implant in the mouth of the patient.

9. The robotic system of claim 8, wherein the virtual model is created without use of a scanning abutment coupled to the dental implant installed in the mouth of the patient.

10. The robotic system of claim 8, wherein the generated positional data is used by one or more processors to modify the pre-operative virtual model of the mouth of the patient to include at least a portion of a virtual model of the installed dental implant.

11. The robotic system of claim 8, wherein in response to the working arm being coupled with a drill-bit tool, the at least a portion of the working arm is further moveable to form an opening in bone within the mouth of the patient to receive the dental implant therein.

12. The robotic system of claim 8, wherein one or more processors of the robotic system are configured to control movement of the working arm to automatically install the dental implant in the mouth of the patient according to a pre-planned installation procedure, wherein the working arm is coupled to a dental-implant-driving tool during the automatic installation.

13. The robotic system of claim 12, wherein at least one of the one or more processors is configured to control movement of the working arm to automatically remove a portion of a jaw bone of the patient, thereby forming a socket for receiving the dental implant, according to the pre-planned installation procedure, wherein the working arm is coupled to a drill-bit tool during the removal.

14. The robotic system of claim 8, wherein a tip of the grounding arm has at least six degrees of freedom relative to the base and wherein a tip of the one or more tools coupled to the working arm has at least six degrees of freedom relative to the base.

15. The robotic system of claim 8, wherein the at least a portion of the working arm is automatically moveable by one or more processors of the robotic system.

16. The robotic system of claim 8, wherein the one or more tools include a drill-bit tool, a dental-implant-driving tool, a rotating mill tool, a saw tool, a probe tool, a scalpel tool, or any combination thereof.

17. A robotic system for use during installation of a dental implant in a mouth of a patient, the robotic system comprising:
   a base;
   a grounding arm extending from the base and being configured to be coupled to a fixed structure within the mouth of the patient for establishing an origin for the robotic system relative to the mouth of the patient;
   a working arm extending from the base and being configured to be coupled with one or more tools for use during the installation of the dental implant, at least a portion of the working arm being movable to install the dental implant in the mouth of the patient;
   one or more sensors to monitor positions of the grounding arm and the working arm, the one or more sensors generating positional data related to the location of the one or more tools relative to the established origin, wherein during the dental surgical procedure, the one or more sensors monitor a position of the grounding arm and the working arm to generate positional data related to the location of the dental-implant-driving tool relative to the established origin; and
   one or more processors configured to:
   determine an invisible boundary wall to be established around a pre-determined location for the dental implant to be installed in the mouth of the patient;
   moving, semi-manually and as part of the dental surgical procedure, at least a portion of a working arm of the robotic system coupled to the one or more tools to install the dental implant in the mouth of the patient;
   during the moving, automatically enforce the determined invisible boundary wall by providing an indication to a user that the working arm of the robotic system is to be moved outside of the determined invisible boundary wall; and
   creating, without scanning, the post-operative virtual model of the at least a portion of the mouth of the patient based on the obtained pre-operative virtual model and the generated positional data, the post-operative virtual model including a virtual dental implant that corresponds to a location and orientation of the dental implant in the mouth of the patient.

18. The method of claim 17, wherein providing the indication to the user can include at least one of:
   preventing the working arm of the robotic system to be moved outside the invisible boundary wall; and
   providing tactile feedback to the user indicating that the working arm is to be moved outside the invisible boundary wall.

19. The method of claim 17, further including:
   displaying to the user a virtual invisible boundary wall relative to the pre-operative virtual model, the virtual invisible boundary wall corresponding to the invisible boundary wall.

* * * * *